US006646132B2

(12) United States Patent
Morishima et al.

(10) Patent No.: US 6,646,132 B2
(45) Date of Patent: Nov. 11, 2003

(54) INFORMATION RECORDING MEDIUM AND NOVEL OXONOL COMPOUND

(75) Inventors: Shin-ichi Morishima, Kanagawa (JP); Michihiro Shibata, Kanagawa (JP); Yoshihisa Usami, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/774,797

(22) Filed: Feb. 1, 2001

(65) Prior Publication Data

US 2002/0009669 A1 Jan. 24, 2002

Related U.S. Application Data

(62) Division of application No. 09/324,054, filed on Jun. 2, 1999, now Pat. No. 6,225,024.

(30) Foreign Application Priority Data

Jun. 4, 1998 (JP) .......................................... 10-156207

(51) Int. Cl.$^7$ ..................... C07D 213/22; C07D 317/34
(52) U.S. Cl. ................. 546/347; 546/347; 430/270.18; 549/372
(58) Field of Search .................... 546/347; 430/270.18; 549/372

(56) References Cited

U.S. PATENT DOCUMENTS

| 3,879,678 A | * | 4/1975 | McColgin et al. ......... 331/94.5 |
| 4,968,593 A | | 11/1990 | Inagaki et al. ............. 430/495 |
| 6,020,105 A | | 2/2000 | Wariishi .................. 430/270.2 |

FOREIGN PATENT DOCUMENTS

| EP | 0 780 443 A2 | 6/1997 | ................... 546/94 |
| EP | 0 833 314 A2 | 4/1998 | ............ 430/270.18 |

OTHER PUBLICATIONS

CAPLUS reference listing, Index Term 56165–82–3 for US Patent 3,879,678, McColgin et al., Apr. 22, 1975.*
A.S. Tatikolov, et al. Photoinduced Electron Transfer in Ion Pairs of Cation–Anion Polymethine Dyes, vol. 44, No. 5, May 1995, pp. 851–857.

XP–002116245—Chemical Abstract, vol. 122 Jun. 12, 1995, No. 24.

XP–002116246—Chemical Abstract, vol. 120 Feb. 7, 1994, No. 6.

XP–002116278—Chemical Abstract, vol. 119, Nov. 15, 1993, No. 20.

* cited by examiner

Primary Examiner—Alan L. Rotman
Assistant Examiner—Janet L Coppins
(74) Attorney, Agent, or Firm—Sughrue Mion, PLLC

(57) ABSTRACT

An information recording medium is disclosed, comprising a substrate having provided thereon a recording layer capable of recording information by a laser ray, wherein the recording layer contains a dye compound represented by formula (I-1):

(I-1)

[Chemical structure showing an oxonol compound with substituents $R_1$, $R_2$, $R_3$, $R_4$, linkers $L_1$, $L_2$, $L_3$, subscript $m$, and counterion $(1/k)X^{k+}$]

wherein $R_1$, $R_2$, $R_3$ and $R_4$ each independently represents a hydrogen atom, a substituted or unsubstituted alkyl group, a substituted or unsubstituted aryl group, a substituted or unsubstituted aralkyl group or a substituted or unsubstituted heterocyclic group, $L_1$, $L_2$ and $L_3$ each independently represents a methine group which may have a substituent, m represents 0, 1, 2 or 3, $X^{k+}$ represents a cation and k represents an integer of from 1 to 10, provided that when m is 2 or 3, the plurality of $L_2$ and $L_3$ groups may be the same or different. Also disclosed is an information recording method using the above-described information recording medium.

1 Claim, No Drawings

INFORMATION RECORDING MEDIUM AND NOVEL OXONOL COMPOUND

This is a divisional of application Ser. No.09/324,054 filed Jun. 2, 1999 now U.S. Pat. No. 6,225,024, the disclosure of which is incorporated herein by reference.

FIELD OF THE INVENTION

The present invention relates to a heat mode-type information recording medium capable of writing (recording) and reading (reproducing) information using a laser ray having a high energy density, and an information recording method using the information recording medium. More specifically, the present invention relates to a heat mode-type information recording medium suitable for the recording of information using a visible laser ray, such as recordable digital video disc (DVD-R).

BACKGROUND OF THE INVENTION

Heretofore, an information recording medium (optical disc) capable of once recording information by a laser ray has been known. This information recording medium is also called a recordable CD (so-called CD-R) and is advantageous in that a small amount of CD can be swiftly provided at a reasonable cost as compared with the manufacturing of conventional CDs. Accordingly, demands for this recording medium are increasing with recent prevalence of personal computers.

A representative structure of the CD-R type information recording medium is such that a recording layer comprising an organic dye, a reflection layer comprising a metal, for example, gold, and a resin-made protective layer are laminated in this order on a transparent disc-like substrate. The recording of information on the optical disc is performed by irradiating a laser ray in the near infrared region (usually, a laser ray at a wavelength in the vicinity of 780 nm) to locally cause exothermic deformation of the recording layer. On the other hand, the reading (reproduction) of the information is usually performed by irradiating a laser ray having the same wavelength as that of the laser ray for recording and thereby detecting the difference in the reflectance between the exothermically deformed portion (recorded area) and the portion free of deformation (unrecorded area) of the recording layer.

Recently, an information recording medium having a higher recording density is demanded. In order to increase the recording density, reduction in the light size of the laser irradiated is effective and it is theoretically known that a laser ray having a short wavelength can be more reduced in the light size and is advantageous in the realization of a higher density. Therefore, studies are being made to develop an optical disc capable of recording and reproducing by a laser ray having a wavelength shorter than 780 nm which has been conventionally used. For example, an optical disc called a recordable digital video disc (so-called DVD-R) has been proposed. This optical disc is produced as follows: a disc is prepared by providing a recording layer comprising a dye on a transparent disc-like substrate having a diameter of 120 mm or 80 mm and having formed thereon a pregroove in a track pitch of 0.8 µm narrower than 1.6 µm of CD-R, and usually by further providing a reflection layer and a protective layer on the recording layer, and thereafter a couple of these discs or this disc and a disc-like protective substrate having almost the same dimension are laminated using an adhesive such that the recording layer is disposed in the inner side. On the DVD-R, the recording and reproduction are performed by irradiating a visible laser ray (a laser ray usually having a wavelength of from 600 to 700 nm), therefore, recording having a density higher than that of CD-R type optical disc can be attained.

The DVD-R type information recording medium can have a recorded information content a few times larger than that of conventional CD-R type information recording mediums, accordingly, the information recording medium is of course demanded to have a high recording sensitivity and in particular, since a large amount of information must be swiftly processed, is demanded to be reduced in the generation ratio of errors even at the high-speed recording.

Furthermore, since the recording layer comprising a dye is generally low in the aging stability against heat or light, a recording layer capable of maintaining stable performance against heat or light for a long period of time is demanded.

JP-A-63-209995 (the term "JP-A" as used herein means an "unexamined published Japanese patent application") (corresponding to U.S. Pat. No. 4,968,593) and European Patent Publication No. 833,314A2 disclose a CD-R type information recording medium comprising a substrate having provided thereon a recording layer comprising an oxonol dye. By using this dye compound, the stable recording/reproduction properties can be maintained for a long period of time. As such a dye compound, an oxonol dye compound where ammonium in the form of a salt is introduced into the molecule is described.

The present inventors studied the performance of a DVD-R type information recording medium using an oxonol dye described in the above-described patent publication. As a result of the extensive investigation, it has been found that the DVD-R type information recording medium containing the oxonol dye in the recording layer exhibits relatively high recording properties but is not satisfied in the recording and reproduction properties because of low reflectance and low degree of modulation. Furthermore, reproduction failures were readily caused when the medium was exposed to light such as sunlight for a long period of time, thus, it was also found that the information recording medium is not satisfied in the light fastness.

SUMMARY OF THE INVENTION

Accordingly, an object of the present invention is to provide an information recording medium having high recording properties, exhibiting high stability (particularly high stability with light fastness) such that its recording properties can be maintained for a long period of time, and ensuring suitable recording and reproduction of information by a visible laser ray.

Another object of the present invention is to provide a method for recording information using the above-described information recording medium.

The present inventors have found that an information recording medium having excellent recording/reproduction properties as compared with conventional information recording mediums and moreover, having high storage stability with further improved light fastness and storage durability can be obtained by using a dye compound represented by formula (I-1) in the recording layer. More specifically, the objects of the present invention can be attained by the following inventions (1) to (5).

(1) An information recording medium comprising a substrate having provided thereon a recording layer capable of recording information by a laser ray, wherein said recording layer contains a dye compound represented by formula (I-1):

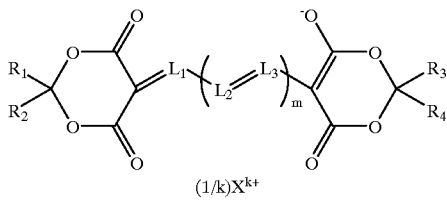

(I-1)

(1/k)X^{k+} wherein $R_1$, $R_2$, $R_3$ and $R_4$ each independently represents a hydrogen atom, a substituted or unsubstituted alkyl group, a substituted or unsubstituted aryl group, a substituted or unsubstituted aralkyl group or a substituted or unsubstituted heterocyclic group, $L_1$, $L_2$ and $L_3$ each independently represents a methine group which may have a substituent, m represents 0, 1, 2 or 3, $X^{k+}$ represents a cation and k represents an integer of from 1 to 10, provided that when m is 2 or 3, the plurality of $L_2$ and $L_3$ groups may be the same or different.

(2) The information recording medium as described in (1) above, wherein $X^{k+}$ is a quaternary ammonium ion.

(3) The information recording medium as described in (1) above, wherein $X^{k+}$ is an onium ion represented by formula (I-2):

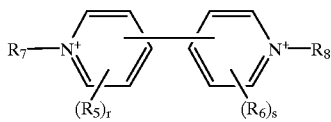

(I-2)

wherein $R_5$ and $R_6$ each independently represents a substituent, $R_7$ and $R_8$ each independently represents a substituted or unsubstituted alkyl group, a substituted or unsubstituted alkenyl group, a substituted or unsubstituted alkynyl group, a substituted or unsubstituted aralkyl group, a substituted or unsubstituted aryl group or a substituted or unsubstituted heterocyclic group, the couples of $R_5$ and $R_6$, $R_5$ and $R_7$, $R_6$ and $R_8$, and $R_7$ and $R_8$ each may be combined together to form a ring, and r and s each independently represents 0 or an integer of from 1 to 4, provided that when r and s each is 2 or more, the plurality of $R_5$ or $R_6$ groups may be the same or different.

(4) An oxonol compound represented by formula (II-1):

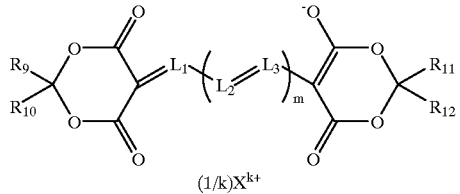

(II-1)

(1/k)X^{k+} wherein $R_9$, $R_{10}$, $R_{11}$ and $R_{12}$ each independently represents a hydrogen atom, a substituted or unsubstituted alkyl group, a substituted or unsubstituted aryl group, a substituted or unsubstituted aralkyl group or a substituted or unsubstituted heterocyclic group, $L_1$, $L_2$ and $L_3$ each represents a methine group which may have a substituent, m represents 0, 1, 2 or 3, $X^{k+}$ represents a cation and k represents an integer of from 1 to 10, provided that when m is 1 or 2, $R_9$, $R_{10}$, $R_{11}$ and $R_{12}$ are not a methine group at the same time, when m is 2, the couples of $R_9$ and $R_{10}$, and $R_{11}$ and $R_{12}$ each does not form a combination of a methyl group and a n-hexyl group, and when m is 2 or 3, the plurality of $L_2$ and $L_3$ groups may be the same or different. In the formula (II-1), $R_9$, $R_{10}$, $R_{11}$, $R_{12}$, $L_1$, $L_2$, $L_3$, m, $X^{k+}$ and k each has substantially the same as those represented by $R_1$ to $R_4$, $L_1$ to $L_3$, m, $X^{k+}$ and k in formula (I-1), with the preferred range thereof being also the same, except for the proviso.

(5) An oxonol compound represented by formula (I-3):

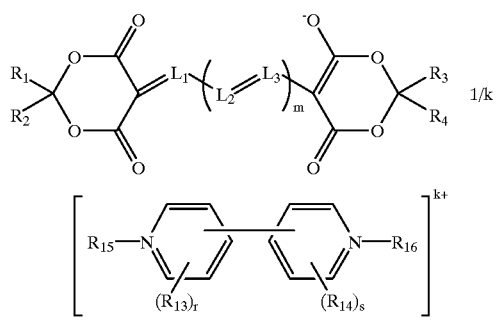

(I-3)

1/k wherein $R_1$, $R_2$, $R_3$ and $R_4$ each independently represents a hydrogen atom, a substituted or unsubstituted alkyl group, a substituted or unsubstituted aryl group, a substituted or unsubstituted aralkyl group or a substituted or unsubstituted heterocyclic group, $L_1$, $L_2$ and $L_3$ each independently represents a methine group which may have a substituent, m represents 0, 1, 2 or 3, $R_{13}$ and $R_{14}$ have the same meanings as the groups represented by $R_5$ and $R_6$ in formula (I-2), respectively, $R_{15}$ and $R_{16}$ each independently represents a substituted or unsubstituted alkyl group having from 1 to 18 carbon atoms, a substituted or unsubstituted alkenyl group having from 2 to 18 carbon atoms, a substituted or unsubstituted alkynyl group having from 2 to 18 carbon atoms, a substituted or unsubstituted aralkyl group having from 7 to 18 carbon atoms, a substituted or unsubstituted aryl group having from 6 to 18 carbon atoms or a substituted or unsubstituted 4-, 5-, 6- or 7-membered heterocyclic group, the couples of $R_{13}$ and $R_{14}$, $R_{13}$ and $R_{15}$, $R_{14}$ and $R_{16}$, and $R_{15}$ and $R_{16}$ each may be combined to form a 4-, 5-, 6- or 7-membered ring, r and s each independently represents 0 or an integer of from 1 to 4 and k represents an integer of from 1 to 10, provided that when r and s each is 2 or more, the plurality of $R_{13}$ or $R_{14}$ groups may be the same or different, and when m is 2 or 3, the plurality of $L_2$ and $L_3$ groups may be the same or different. In the formula (I-3), $R_1$ to $R_4$, $L_1$ to $L_3$ and k are as defined in formula (I-1) and $R_{13}$ to $R_{14}$, r and s each has substantially the same as those represented by $R_5$ to $R_8$, r and s in formula (I-2), with the preferred range thereof being also the same.

The present invention is preferably a heat mode-type information recording medium having a thickness of 1.2±0.2 mm, which is obtained by combining two sheets of laminates each comprising a transparent disc-like substrate having provided thereon a recording layer such that respective recording layers are disposed in the inner side, the disc-like substrate having a diameter of 120±3 mm or 80±3 mm and a thickness of 0.6±0.1 mm and having formed thereon a pregroove in a track pitch of from 0.6 to 0.9 μm, and the recording layer comprising a dye compound represented by the following formula (I-1) and being provided on the side having the pregroove of the substrate, or by combining a laminate comprising a transparent disc-like substrate having provided thereon a recording layer with a disc-like protective substrate such that the recording layer is disposed in the inner side, the disc-like substrate having a diameter of 120±3 mm or 80±3 mm and a thickness of 0.6±0.1 mm and having formed thereon a pregroove in a track pitch of from 0.6 to 0.9 μm, and the recording layer comprising a dye compound represented by the following formula (I-1) and being provided on the side having the pregroove of the substrate:

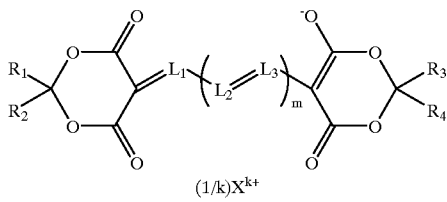

(I-1)

wherein $R_1$, $R_2$, $R_3$ and $R_4$ each independently represents a hydrogen atom, an alkyl group, an aryl group, an aralkyl group or a heterocyclic group, $L_1$, $L_2$ and $L_3$ each independently represents a methine group which may have a substituent, m represents 0, 1, 2 or 3, $X^{k+}$ represents a cation and k represents an integer of from 1 to 10, provided that when m is 2 or 3, the plurality of $L_2$ and $L_3$ groups may be the same or different.

Furthermore, the present invention is preferably an information recording method comprising irradiating a laser ray having a wavelength of from 600 to 700 nm on the above-described information recording medium to record information.

Preferred embodiments of the information recording medium of the present invention are described below.

(1) In the formula (I-1), $X^{k+}$ is a quaternary ammonium ion.

(2) In the formula (I-1), k is from 1 to 4.

(3) In the formula (I-1), k is 2.

(4) In the formula (I-1), $X^{k+}$ is an onium ion represented by formula (I-2):

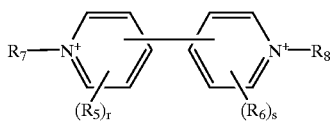

(I-2)

wherein $R_5$ and $R_6$ each independently represents a substituent, $R_7$ and $R_8$ each independently represents an alkyl group, an alkenyl group, an alkynyl group, an aralkyl group, an aryl group or a heterocyclic group, the couples of $R_5$ and $R_6$, $R_5$ and $R_7$, $R_6$ and $R_8$, and $R_7$ and $R_8$ each may be combined together to form a ring, and r and s each independently represents 0 or an integer of from 1 to 4, provided that when r and s each is 2 or more, the plurality of $R_5$ or $R_6$ groups may be the same or different.

(5) A reflective layer is further provided on the recording layer.

(6) In the above (5), a protective layer is further provided on the reflective layer.

DETAILED DESCRIPTION OF THE INVENTION

The present invention is described in detail below.

The compound represented by formula (I-1) of the present invention is described in detail.

In the formula, $R_1$, $R_2$, $R_3$ and $R_4$ each independently represents a hydrogen atom, an alkyl group, an aryl group, an aralkyl group or a heterocyclic group. The alkyl group includes an alkyl group having from 1 to 20 carbon atoms (e.g., methyl, ethyl, propyl, butyl, i-butyl, t-butyl, i-amyl, cyclopropyl, hexyl) and may have a substituent described below (exclusive of an alkyl group).

Examples of the substituent (hereinafter, referred to as "substituent SUB-1") include an alkyl group having from 1 to 20 carbon atoms (e.g., methyl, ethyl, propyl, carboxymethyl, ethoxycarbonylmethyl), an aralkyl group having from 7 to 20 carbon atoms (e.g., benzyl, phenethyl), an alkoxy group having from 1 to 8 carbon atoms (e.g., methoxy, ethoxy), an aryl group having from 6 to 20 carbon atoms (e.g., phenyl, naphthyl), an aryloxy group having from 6 to 20 carbon atoms (e.g., phenoxy, naphthoxy), a heterocyclic group (e.g., pyridyl, pyrimidyl, pyridazyl, benzimidazolyl, benzothiazolyl, benzoxazolyl, 2-pyrrolidinon-1-yl, 2-piperidon-1-yl, 2,4-dioxyimidazolidin-3-yl, 2,4-dioxyoxazolidin-3-yl, succinimido, phthalimido, maleimido), a halogen atom (e.g., fluorine, chlorine, bromine, iodine), a carboxyl group, an alkoxycarbonyl group having from 2 to 10 carbon atoms (e.g., methoxycarbonyl, ethoxycarbonyl), a cyano group, an acyl group having from 2 to 10 carbon atoms (e.g., acetyl, pivaloyl), a carbamoyl group having from 1 to 10 carbon atoms (e.g., carbamoyl, methylcarbamoyl, morpholinocarbamoyl), an amino group, a substituted amino group having from 1 to 20 carbon atoms (e.g., dimethylamino, diethylamino, bis(methylsulfonylethyl)amino, N-ethyl-N'-sulfoethylamino), a sulfo group, a hydroxyl group, a nitro group, a sulfonamido group having from 1 to 10 carbon atoms (e.g., methanesulfonamido), a ureido group having from 1 to 10 carbon atoms (e.g., ureido, methylureido), a sulfonyl group having from 1 to 10 carbon atoms (e.g., methanesulfonyl, ethanesulfonyl), a sulfinyl group having from 1 to 10 carbon atoms (e.g., methanesulfinyl) and a sulfamoyl group having from 0 to 10 carbon atoms (e.g., sulfamoyl, methanesulfamoyl). The carboxyl group and the sulfo group each may be in the form of a salt.

The aryl group represented by $R_1$, $R_2$, $R_3$ or $R_4$ includes an aryl group having from 6 to 20 carbon atoms (e.g., phenyl, naphthyl) and may have the substituent SUB-1 described above.

The aralkyl group represented by $R_1$, $R_2$, $R_3$ or $R_4$ includes an aralkyl group having from 7 to 20 carbon atoms (e.g., benzyl, phenethyl) and may have the substituent SUB-1 described above.

The heterocyclic group represented by $R_1$, $R_2$, $R_3$ or $R_4$ includes a 5- or 6-membered saturated or unsaturated heterocyclic group consisting of a carbon atom, a nitrogen atom, an oxygen atom or a sulfur atom and examples thereof include a pyridyl group, a pyrimidyl group, a pyridazyl group, a piperidyl group, a triazyl group, a pyrrolyl group, an imidazolyl group, a triazolyl group, a furanyl group, a thiophenyl group, a thiazolyl group, an oxazolyl group, an isothiazolyl group, an isooxazolyl group, and a benzo-condensed ring thereof (e.g., quinolyl group, benzimidazolyl group, benzothiazolyl group, benzoxazolyl group). The heterocyclic ring may have the substituent SUB-1 described above.

$R_1$, $R_2$, $R_3$ and $R_4$ each is preferably an alkyl group having from 1 to 8 carbon atoms, an aryl group having from 6 to 10 carbon atoms, an aralkyl group having from 7 to 10 carbon atoms or a heterocyclic group having from 6 to 10 carbon atoms.

When $R_1$ and $R_2$ or $R_3$ and $R_4$ each is an alkyl group, $R_1$ and $R_2$ or $R_3$ and $R_4$ may be combined to form a carbocyclic ring (e.g., cyclopropyl, cyclobutyl, cyclopentyl, cyclohexyl, 2-methylcyclohexyl, cycloheptyl, cyclooctyl) or a heterocyclic ring (e.g., piperidyl, chromanyl, morpholyl), preferably a carbocyclic ring having from 3 to 10 carbon atoms or a heterocyclic ring having from 2 to 10 carbon atoms.

In the formulae (I-1) and (II-1), the couples of $R_1$ and $R_2$ and/or $R_3$ and $R_4$ or the couples of $R_9$ and $R_{10}$ and/or $R_{11}$ and $R_{12}$ each is preferably combined together to form a ring from the viewpoint of wet heat stability.

$L_1$, $L_2$ and $L_3$ each independently represents a substituted or unsubstituted methine group. Examples of the substituent include those described above as the substituent SUB-1. $L_1$, $L_2$ and $L_3$ each is preferably an unsubstituted methine group, an alkyl-substituted methine group having from 1 to 5 carbon atoms, an aralkyl-substituted methine group having from 7 to 10 carbon atoms, an aryl-substituted methine group having from 6 to 10 carbon atoms, a saturated or unsaturated heterocyclic ring-substituted methine group or a halogen-substituted methine group. m represents 0, 1, 2 or 3, preferably 1, 2 or 3.

The cation moiety is described in detail below.

Examples of the cation represented by $X^{k+}$ include hydrogen ion, metal ions such as sodium ion, potassium ion, lithium ion, calcium ion, iron ion and copper ion, a metal complex ion, ammonium ion, pyridinium ion, oxonium ion, sulfonium ion, phosphonium ion, selenonium ion and iodonium ion. $X^{k+}$ is preferably not a cyanine dye. $X^{k+}$ is preferably a quaternary ammonium ion.

The quaternary ammonium is generally obtained by alkylating (Menshutkin reaction), alkenylating, alkynylating or arylating a tertiary amine (e.g., trimethylamine, triethylamine, tributylamine, triethanolamine, N-methylpyrrolidine, N-methylpiperidine, N,N-dimethylpiperazine, triethylenediamine, N,N,N',N'-tetramethylethylenediamine) or a nitrogen-containing heterocyclic ring (e.g., pyridine ring, picoline ring, 2,2'-bipyridyl ring, 4,4'-bipiridyl ring, 1,10-phenanthroline ring, quinoline ring, oxazole ring, thiazole ring, N-methylimidazole ring, pyrazine ring, tetrazole ring).

The quaternary ammonium ion represented by $X^{k+}$ is preferably a quaternary ammonium ion comprising a nitrogen-containing heterocyclic ring, more preferably a quaternary pyridinium ion.

k represents an integer of from 1 to 10, preferably from 1 to 4, more preferably 2.

The onium ion represented by $X^{k+}$ is preferably an onium ion represented by formula (I-2) shown below. Usually, this compound can be easily obtained by the Menshutkin reaction of 2,2'-bipyridyl or 4,4'-bipiridyl with a halide having an objective substituent (see, for example, JP-A-61-148162) or an arylation reaction according to the method described in JP-A-51-16675 and JP-A-1-96171.

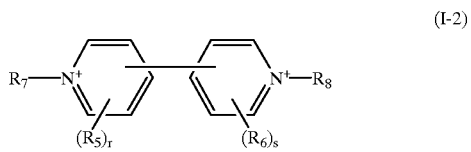

wherein $R_5$ and $R_6$ each independently represents a substituent, $R_7$ and $R_8$ each independently represents an alkyl group, an alkenyl group, an alkynyl group, an aralkyl group, an aryl group or a heterocyclic group, the couples of $R_5$ and $R_6$, $R_5$ and $R_7$, $R_6$ and $R_8$, and $R_7$ and $R_8$ each may be combined together to form a ring, and r and s each independently represents 0 or an integer of from 1 to 4, provided that when r and s each is 2 or more, the plurality of $R_5$ or $R_6$ groups may be the same or different.

The alkyl group represented by $R_7$ or $R_8$ is preferably a substituted or unsubstituted alkyl group having from 1 to 18 carbon atoms, more preferably a substituted or unsubstituted alkyl group having from 1 to 8 carbon atoms, which may be linear, branched or cyclic. Examples thereof include methyl, ethyl, n-propyl, isopropyl, n-butyl, isobutyl, t-butyl, n-hexyl, neopentyl, cyclohexyl, adamantyl and cyclopropyl.

Examples of the substituent (hereinafter, referred to as "substituent SUB-2") for the alkyl group include the followings:

a substituted or unsubstituted alkenyl group having from 2 to 18 (preferably from 2 to 8) carbon atoms (e.g., vinyl);

a substituted or unsubstituted alkynyl group having from 2 to 18 (preferably from 2 to 8) carbon atoms (e.g., ethynyl);

a substituted or unsubstituted aryl group having from 6 to 10 carbon atoms (e.g., phenyl, naphthyl);

a halogen atom (e.g., F, Cl, Br);

a substituted or unsubstituted alkoxy group having from 1 to 18 (preferably from 1 to 8) carbon atoms (e.g., methoxy, ethoxy);

a substituted or unsubstituted aryloxy group having from 6 to 10 carbon atoms (e.g., phenoxy, p-methoxyphenoxy);

a substituted or unsubstituted alkylthio group having from 1 to 18 (preferably from 1 to 8) carbon atoms (e.g., methylthio, ethylthio);

a substituted or unsubstituted arylthio group having from 6 to 10 carbon atoms (e.g., phenylthio);

a substituted or unsubstituted aryl group having from 2 to 18 (preferably from 2 to 8) carbon atoms (e.g., acetyl, propionyl);

a substituted or unsubstituted alkylsulfonyl or arylsulfonyl group having from 1 to 18 (preferably from 1 to 8) carbon atoms (e.g., methanesulfonyl, p-toluenesulfonyl);

a substituted or unsubstituted acyloxy group having from 2 to 18 (preferably from 2 to 8) carbon atoms (e.g., acetoxy, propionyloxy);

a substituted or unsubstituted alkoxycarbonyl group having from 2 to 18 (preferably from 2 to 8) carbon atoms (e.g., methoxycarbonyl, ethoxycarbonyl);

a substituted or unsubstituted aryloxycarbonyl group having from 7 to 11 carbon atoms (e.g., naphthoxycarbonyl);

an unsubstituted amino group and a substituted amino group having from 1 to 18 (preferably from 1 to 8) carbon atoms (e.g., methylamino, dimethylamino, diethylamino, anilino, methoxyphenylamino, chlorophenylamino, pyridylamino, methoxycarbonylamino, n-butoxycarbonylamino, phenoxycarbonylamino, methylcarbamoylamino, ethylthiocarbamoylamino, phenylcarbamoylamino, acetylamino, ethylcarbonylamino, ethylthiocarbamoylamino, cyclohexylcarbonylamino, benzoylamino, chloroacetylamino, methylsulfonylamino);

a substituted or unsubstituted carbamoyl group having from 1 to 18 (preferably from 1 to 8) carbon atoms (e.g., unsubstituted carbamoyl, methylcarbamoyl, ethylcarbamoyl, n-butylcarbamoyl, t-butylcarbamoyl, dimethylcarbamoyl, morpholinocarbamoyl, pyrrolidinocarbamoyl);

an unsubstituted sulfamoyl group and a substituted sulfamoyl group having from 1 to 18 (preferably from 1 to 8) carbon atoms (e.g., methylsulfamoyl, phenylsulfamoyl);

a cyano group; a nitro group; a carboxy group; a hydroxyl group; and a heterocyclic group (e.g., oxazole ring, benzoxazole ring, thiazole ring, benzothiazole ring, imidazole ring, benzimidazole ring, indolenine ring, pyridine ring, piperidine ring, pyrrolidine ring, morpholine ring, sulfolane ring, furan ring, thiophene ring, pyrazole ring, pyrrole ring, chroman ring, coumarin ring).

The alkenyl group represented by $R_7$ or $R_8$ is preferably a substituted or unsubstituted alkenyl group having from 2 to 18 carbon atoms, more preferably a substituted or unsubstituted alkenyl group having from 2 to 8 carbon atoms, and examples thereof include vinyl, allyl, 1-propenyl and 1,3-butadienyl.

Examples of the substituent for the alkenyl group include preferably those described above as the substituent SUB-2 of the alkyl group.

The alkynyl group represented by $R_7$ or $R_8$ is preferably a substituted or unsubstituted alkynyl group having from 2 to 18 carbon atoms, more preferably a substituted or unsubstituted alkynyl group having from 2 to 8 carbon atoms, and examples thereof include ethynyl and 2-propynyl.

The substituent of the alkynyl group is preferably a substituent described above as the substituent SUB-2 of the alkyl group.

The aralkyl group represented by $R_7$ or $R_8$ is preferably a substituted or unsubstituted aralkyl group having from 7 to 18 carbon atoms, and examples thereof include benzyl and methylbenzyl.

The substituent of the aralkyl group is preferably a substituent described above as the substituent SUB-2 of the alkyl group.

The aryl group represented by $R_7$ or $R_8$ is preferably a substituted or unsubstituted aryl group having from 6 to 18 carbon atoms, and examples thereof include phenyl and naphthyl.

The substituent of the aryl group is preferably a substituent described above as the substituent SUB-2 of the alkyl group or an alkyl group (e.g., methyl, ethyl).

The heterocyclic group represented by $R_7$ or $R_8$ is a 5- or 6-membered saturated or unsaturated heterocyclic ring consisting of a carbon atom, a nitrogen atom, an oxygen atom or a sulfur atom, and examples thereof include an oxazole ring, a benzoxazole ring, a thiazole ring, a benzothiazole ring, an imidazole ring, a benzimidazole ring, an indolenine ring, a pyridine ring, a piperidine ring, a pyrrolidine ring, a morpholine ring, a sulfolane ring, a furan ring, a thiophene ring, a pyrazole ring, a pyrrole ring, a chroman ring and a coumarin ring. The heterocyclic group may be substituted and in this case, the substituent is preferably a substituent described above as the substituent SUB-2 of the alkyl group.

The substituent represented by $R_5$ or $R_6$ has the same meaning as the substituent SUB-2 of the alkyl group or may be an alkyl group (e.g., methyl, ethyl).

In the present invention, the substituent represented by $R_5$ or $R_6$ is preferably a hydrogen atom or an alkyl group, more preferably a hydrogen atom.

The cation moiety of formula (I-2) is more preferably represented by the following formula (I-4) or (I-5):

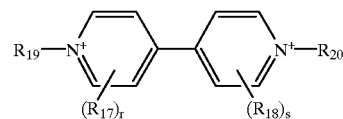

(I-4)

wherein $R_{17}$ and $R_{18}$ each has the same meaning as the substituent represented by $R_5$ or $R_6$, with the preferred range thereof being also the same, $R_{19}$ and $R_{20}$ each has the same meaning as the substituent represented by $R_7$ or $R_8$, with the preferred range thereof being also the same, and r and s each independent represents 0 or an integer of from 1 to 4, provided that when r and s each is 2 or more, the plurality of $R_{17}$ or $R_{18}$ groups may be the same or different;

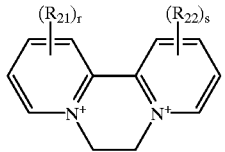

(I-5)

wherein $R_{21}$ and $R_{22}$ each has the same meaning as the substituent represented by $R_5$ or $R_6$, with the preferred range thereof being also the same, or $R_{21}$ and $R_{22}$ are preferably combined with each other to form a carbocyclic or heterocyclic ring, more preferably a condensed aromatic ring with respective pyridine rings to which $R_{21}$ and $R_{22}$ are bonded, and r and s each independent represents 0 or an integer of from 1 to 4, provided that when r and s each is 2 or more, the plurality of $R_{21}$ or $R_{22}$ groups may be the same or different.

Specific examples of the anion moiety (shown by [A-]) and the cation moiety (shown by [B-]) of the dye compound represented by formula (I-1) for use in the present invention are set forth below.

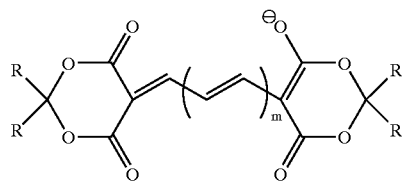
| No. | R | m |
|---|---|---|
| A-1 | H | 3 |
| A-2 | " | 2 |
| A-3 | " | 1 |
| A-4 | CH₃ | 3 |
| A-5 | " | 2 |
| A-6 | " | 1 |
| A-7 | " | 0 |
| A-8 | C₂H₅ | 3 |
| A-9 | " | 2 |
| A-10 | C₃H₇ | 3 |
| A-11 | " | 2 |
| A-12 | " | 1 |
| A-13 | —CH₂—C(CH₃)₃ | 3 |
| A-14 | —CH₂CH(CH₃)₂ | 3 |
| A-15 | " | 2 |
| A-16 | " | 1 |
| A-17 | cyclopropyl | 3 |
| A-18 | cyclohexyl | 3 |
| A-19 | cyclohexyl | 2 |
| A-20 | —CF₃ | 3 |
| A-21 | " | 2 |
| A-22 | " | 1 |
| A-23 | —CH=C(CH₃)₂ | 2 |
| A-24 | —CH₂Cl | 2 |
| A-25 | —CH₂OH | 2 |
| A-26 | " | 3 |
| A-27 | —CH₂CH₂OH | 3 |
| A-28 | " | 2 |
| A-29 | " | 1 |
| A-30 | —CH₂CH₂OCH₃ | 2 |
| A-31 | " | 3 |
| A-32 | —CH₂CH₂N(CH₃)₂ | 2 |
| A-33 | Ph | 2 |
| A-34 | " | 3 |
| A-35 | —CH₂Ph | 2 |

-continued
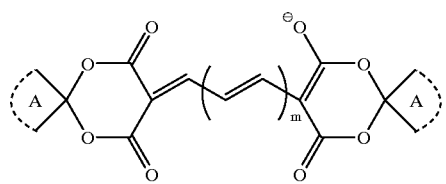
| No. | A | m |
|---|---|---|
| A-36 | cyclopentyl | 2 |
| A-37 | cyclohexyl | 2 |
| A-38 | cyclohexyl | 3 |
| A-39 | methylcyclohexyl | 3 |
| A-40 | methylcyclohexyl | 2 |
| A-41 | methylcyclohexyl | 1 |
| A-42 | methylcyclohexyl | 0 |
| A-43 | dimethylcyclohexyl | 3 |
| A-44 | 4-methyl-1-(propan-2-yl)cyclohexyl | 3 |

-continued
| | | |
|---|---|---|
| A-45 | 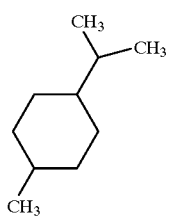 | 2 |
| A-46 | 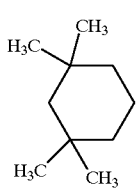 | 2 |
| A-47 | 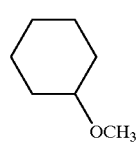 | 2 |
| A-48 | 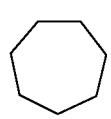 | 2 |
| A-49 | 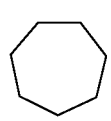 | 3 |
| A-50 |  | 2 |
| A-51 | 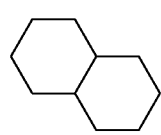 | 2 |
| A-52 | 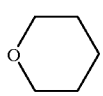 | 2 |
| A-53 | 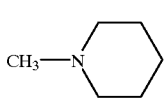 | 2 |
| A-54 | 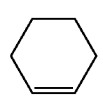 | 2 |

-continued
| | | |
|---|---|---|
| A-55 | 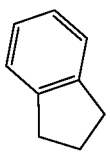 | 2 |
| A-56 | 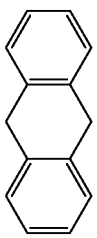 | 2 |
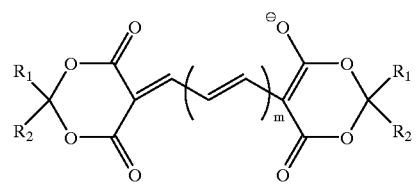
| No. | $R_1$ | $R_2$ | m |
|---|---|---|---|
| A-57 | $CH_3$ | $C_2H_5$ | 3 |
| A-58 | " | Ph | 2 |
| A-59 | $C_2H_5$ | —$CH(CH_3)_2$ | 2 |
| A-60 | $CH_3$ | " | 3 |
| A-61 | " | $C(CH_3)_3$ | 3 |
| A-62 | " | " | 2 |
| A-63 | " | —$CH_2CH(CH_3)_2$ | 2 |
| A-64 | " | 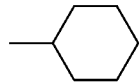 | 3 |
| A-65 | " | —$CH_2CH_2CH(CH_3)_2$ | 2 |
| A-66 | $C_2H_5$ | n-$C_7H_5$ | 2 |
| A-67 | $CH_3$ | —$CH$=$C(CH_3)_2$ | 2 |
| A-68 | " | $CF_3$ | 2 |
| A-69 | " | 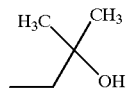 | 2 |
| A-70 | " | 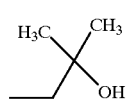 | 3 |
| A-71 | " | $CH_2CH_2NHSO_2CH_3$ | 2 |
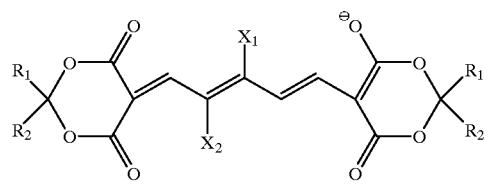
| No. | $R_1$ | $R_2$ | $X_1$ | $X_2$ |
|---|---|---|---|---|
| A-72 | $CH_3$ | $CH_3$ | $CH_3$ | H |
| A-73 | " | " | Ph | " |

-continued
| | | | | |
|---|---|---|---|---|
| A-74 | " | " | OCH$_3$ | " |
| A-75 | " | 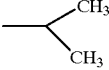 | OPh | " |
| A-76 | " | CH$_3$ | 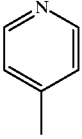 | " |
| A-77 | " | " | C$_2$H$_5$ | " |
| A-78 | " | " | 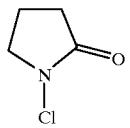 | " |
| A-79 | " | " | Cl | " |
| A-80 | " | " | 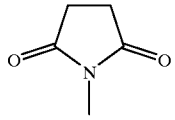 | " |
| A-81 | " | " | 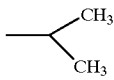 | " |
| A-82 | " | " | H | CH$_3$ |
| A-83 | " | " | " | Ph |
| A-84 | " | " | 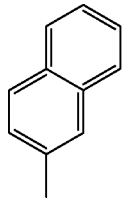 | H |
| A-85 | " | " | —CH$_2$Ph | " |
| A-86 | " | CH$_2$CO$_2$C$_2$H$_5$ | CH$_3$ | CH$_3$ |
A-87
A-88

-continued
A-89
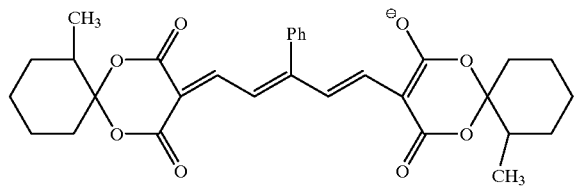
A-90
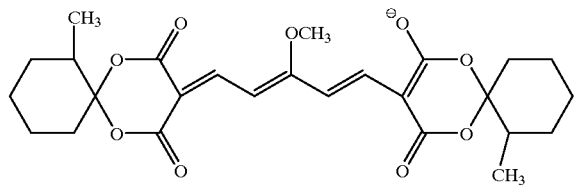
A-91
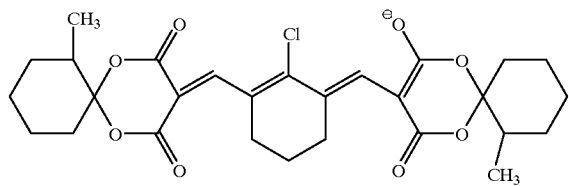
A-92
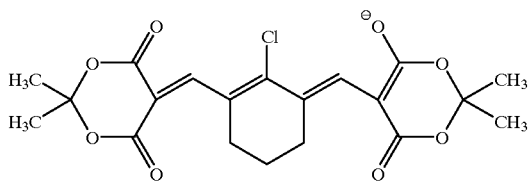
A-93
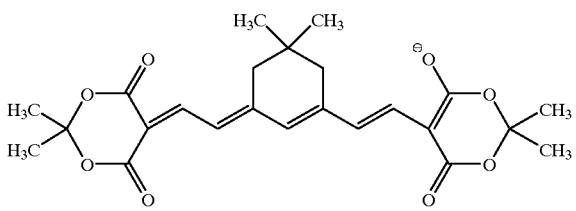
A-94
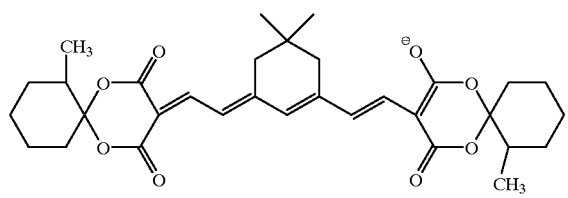
A-95

-continued
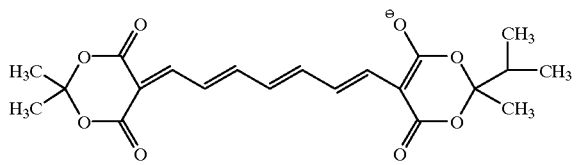
A-96
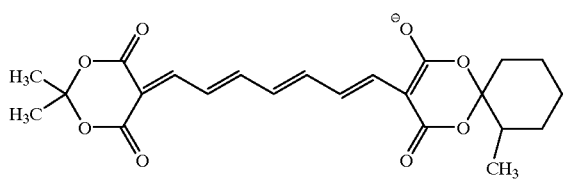
| B-1 | B-2 | B-3 | B-4 | B-5 | B-6 | B-7 |
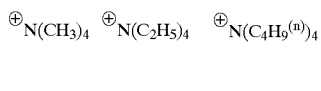 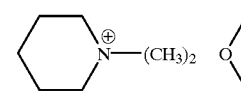 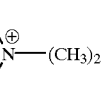 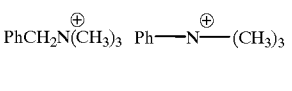
| B-8 | B-9 | | B-10 | B-11 |
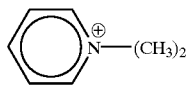 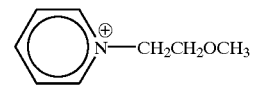 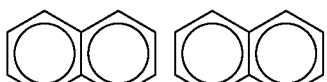
| B-12 | B-13 | B-14 | B-15 | B-16 |
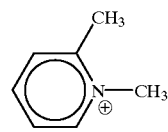 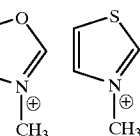 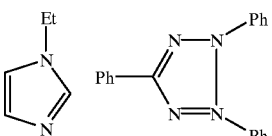
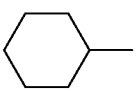 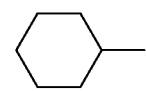
| No. | R¹ | R² |
| --- | --- | --- |
| B-17 | $CH_3$ | $CH_3$ |
| B-18 | $C_2H_5$ | $C_2H_5$ |
| B-19 | $n\text{-}C_3H_7$ | $n\text{-}C_3H_7$ |
| B-20 | $n\text{-}C_4H_9$ | $n\text{-}C_4H_9$ |
| B-21 | $iso\text{-}C_4H_9$ | $iso\text{-}C_4H_9$ |
| B-22 | $n\text{-}C_6H_{13}$ | $n\text{-}C_6H_{13}$ |
| B-23 | $C(CH_3)_3$ | $C(CH_3)_3$ |
| B-24 | $-CH_2CH_2C(CH_3)_3$ | $CH_2CH_2C(CH_3)_3$ |
| B-25 | $CH_2{=}CH$ | $CH_2{=}CH$ |
| B-26 | $NCCH_2$ | $NCCH_2$ |
| B-27 | $EtO_2C{-}CH_2$ | $EtO_2C{-}CH_2$ |
| B-28 | $HOCH_2CH_2$ | $HOCH_2CH_2$ |
| B-29 | $EtOCH_2CH_2$ | $EtOCH_2CH_2$ |
| B-30 | cyclohexyl | cyclohexyl |
| B-31 | $CH_3$ | $PhCH_2$ |

-continued

| | | |
|---|---|---|
| B-32 | CH₃COCH₂ | CH₃COCH₂ |
| B-33 | adamantyl | adamantyl |
| B-34 | CF₃CH₂ | CF₃CH₂ |
| B-35 | Ph | Ph |
| B-36 | 4-CH₃-C₆H₄- | 4-CH₃-C₆H₄- |
| B-37 | 4-CH₃O-C₆H₄- | 4-CH₃O-C₆H₄- |
| B-38 | 4-F-C₆H₄- | 4-F-C₆H₄- |
| B-39 | 4-NC-C₆H₄- | 4-NC-C₆H₄- |
| B-40 | 3-O₂N-C₆H₄- | 3-O₂N-C₆H₄- |

B-41

$[(CH_3)_3N-CH_2-CH_2-N(CH_3)_3]^{2+}$

B-42

$[(CH_3)_3N-(CH_2)_6-N(CH_3)_3]^{2+}$

B-43

$[(CH_3)_3N-CH_2-CH_2-CH_2-O-CH_2-CH_2-O-CH_2-CH_2-CH_2-N(CH_3)_3]^{2+}$

B-44

$$\left[(CH_3)_3N-CH_2-CH_2-\underset{CH_3}{\overset{CH_3}{N}}-CH_2-CH_2-N(CH_3)_3\right]^{3+}$$

B-45

$[(C_4H_9)(CH_3)_2N-CH_2-CH_2-N(CH_3)_2(C_4H_9)]^{2+}$

B-46

$$\left[\text{Py}-CH_2-CH_2-\text{Py}\right]^{2+}$$

B-47

-continued
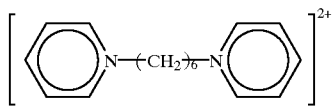
B-49
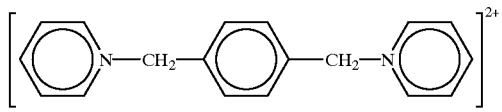
B-50   B-51
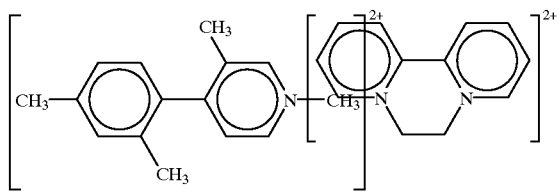
B-52   B-53
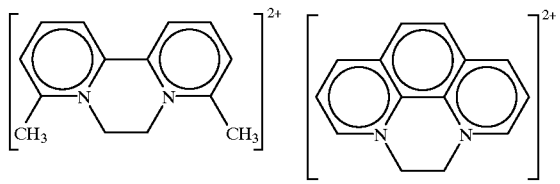
B-54   B-55
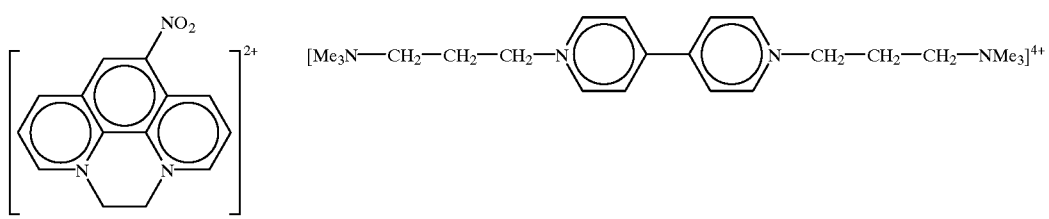
B-56
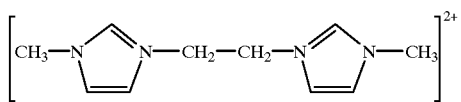
B-57   B-58
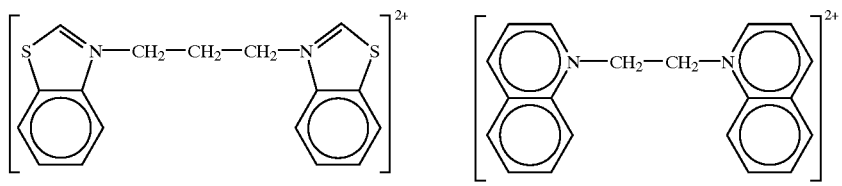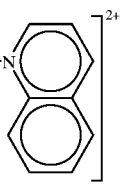
B-59   B-60

-continued
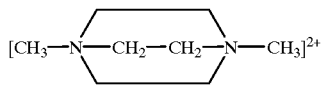 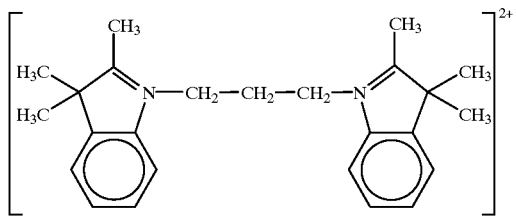
B-61
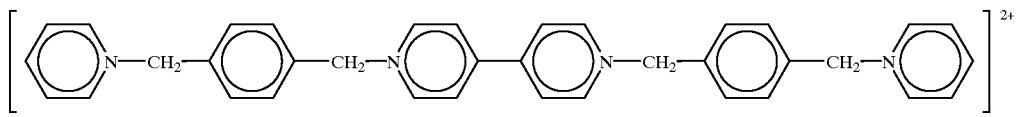
B-62
| B-62 | B-63 | B-64 | B-65 | B-66 | B-67 | B-68 |
|---|---|---|---|---|---|---|
| $Ph_3PMe^{\oplus}$ | $C_{16}H_{33}P(C_2H_5)_3^{\oplus}$ | $Ph_4P^{\oplus}$ | $(C_4H_9)_4P^{\oplus}$ | $Ph\text{—}I^{\oplus}\text{—}Ph$ | $Me_3S^{\oplus}$ | 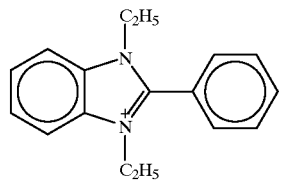 |
B-69          B-70
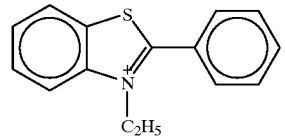    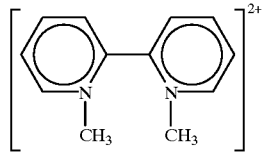
B-71          B-72
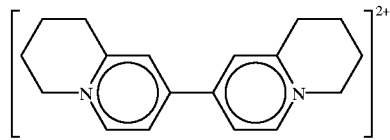    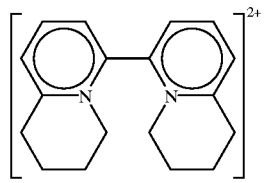
B-73          B-74
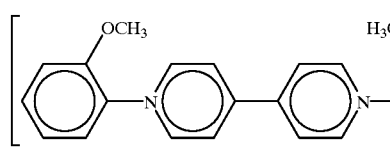    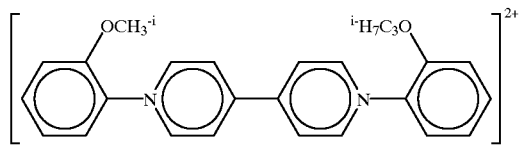
B-75          B-76
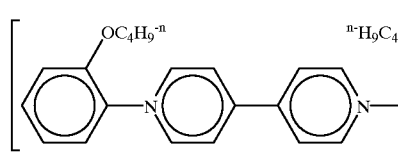    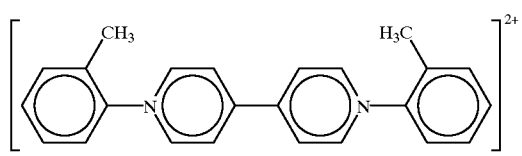
B-77

-continued
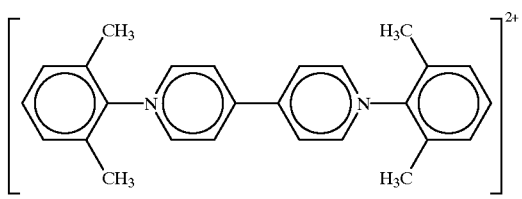
B-78
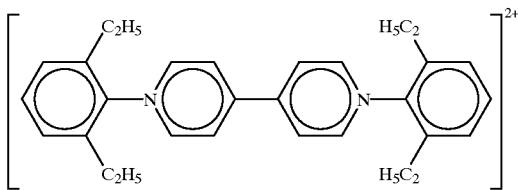
B-80
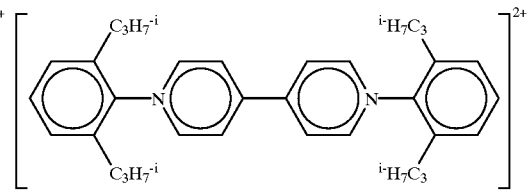
B-79
B-81
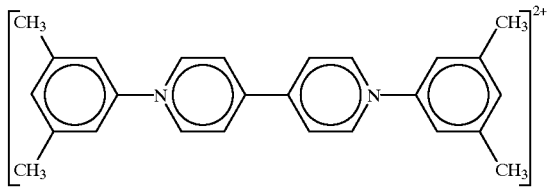
B-82
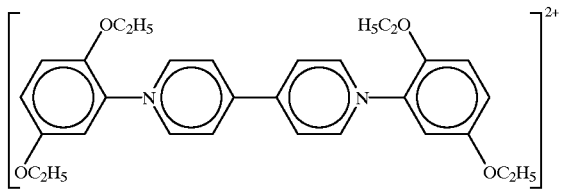
B-83
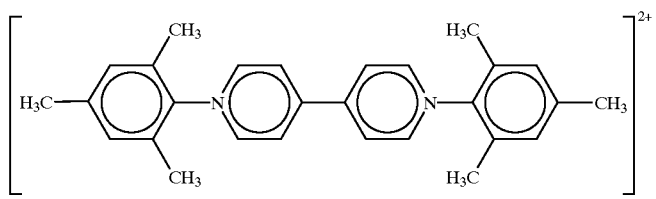
B-84

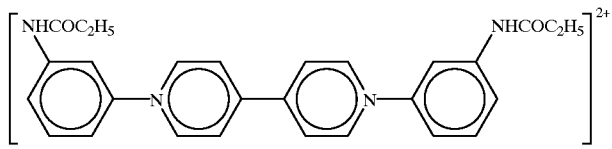
B-85
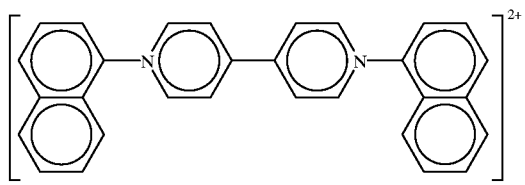
B-86
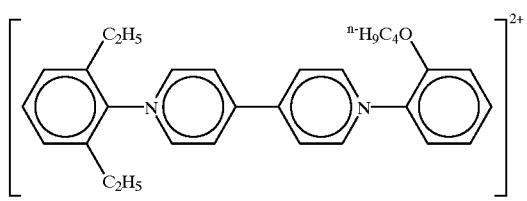
B-87
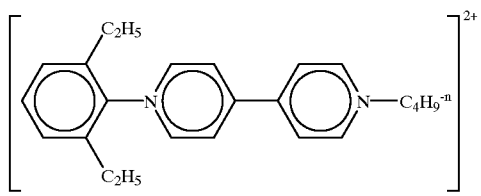
B-88
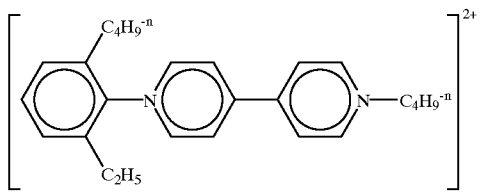
| B-89 | B-90 | B-91 | B-92 | B-93 |
|---|---|---|---|---|
| H⁺ | Li⁺ | Na⁺ | K⁺ | Cu²⁺ |
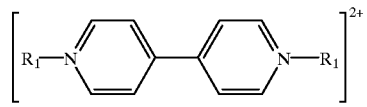
| No. | $R_1$ |
|---|---|
| B-94 | iso-$C_5H_{11}$ |
| B-95 | $CH_3CH_2CH_2CH_2CHCH_2$<br>$\quad\quad\quad\quad\quad\quad\quad\;\;|$<br>$\quad\quad\quad\quad\quad\quad\quad C_2H_5$ |

-continued
| | |
|---|---|
| B-96 | 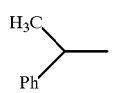 |
| B-97 | PhCH$_2$CH$_2$ |
| B-98 | 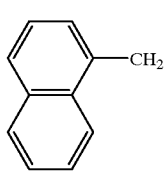 |
| B-99 | 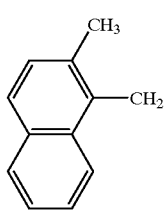 |
| B-100 | 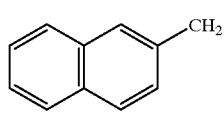 |
| B-101 | 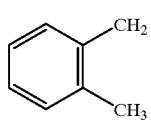 |
| B-102 | 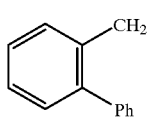 |
| B-103 | CH$_2$=CH—CH$_2$ |
| B-104 | 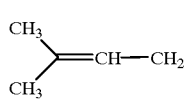 |
| B-105 | 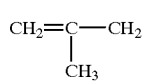 |
| B-106 | Ph$_3$C |
| B-107 | 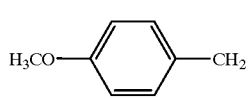 |
| B-108 | CH≡C—CH$_2$ |
| B-109 | CH$_3$SO$_2$CH$_2$CH$_2$ |
| B-110 | 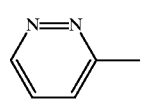 |
| B-111 | 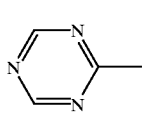 |

-continued $$\left[ R_1-N\underset{}{\overset{}{\bigcirc}}-\underset{}{\overset{}{\bigcirc}}N-R_2 \right]^{2+}$$

| No. | $R_1$ | $R_2$ |
|---|---|---|
| B-112 | 2,4-diamino-6-methyl-1,3,5-triazin-yl | 2,4-diamino-6-methyl-1,3,5-triazin-yl |
| B-113 | 2-methylpyrimidinyl | 2-methylpyrimidinyl |
| B-114 | furan-2-yl-CH₂ | furan-2-yl-CH₂ |
| B-115 | 2,4-dinitrophenyl-methyl | 2,4-dinitrophenyl-methyl |
| B-116 | 2-methylbenzothiazolyl | 2-methylbenzothiazolyl |
| B-118 | iso-C₄H₉ | PhCH₂ |

| B-119 | B-120 | B-121 | B-122 | B-123 | B-124 | B-125 |
|---|---|---|---|---|---|---|
| $H-\overset{H}{\underset{H}{N^{\oplus}}}-H$ | $H-\overset{H}{\underset{H}{N^{\oplus}}}-CH_3$ | $H-\overset{H}{\underset{H}{N^{\oplus}}}-C_2H_5$ | $H-\overset{H}{\underset{C_2H_5}{N^{\oplus}}}-C_2H_5$ | $H_5C_2-\overset{C_2H_5}{\underset{C_2H_5}{N^{\oplus}}}-C_2H_5$ | $PhCH_2-\overset{H}{\underset{CH_3}{N^{\oplus}}}-CH_3$ | $H_9C_4-\overset{H}{\underset{C_4H_9}{N^{\oplus}}}-C_4H_9$ |

| B-126 | B-127 | B-128 | B-129 | B-130 |
|---|---|---|---|---|
| $HON^{\oplus}H\begin{matrix}C_8H_{17}\\C_8H_{17}\end{matrix}$ | $HON^{\oplus}\begin{matrix}H\\C_8H_{17}\\H\end{matrix}$ | $\begin{matrix}C_6H_{13}\\C_6H_{13}\end{matrix}CH-N^{\oplus}H NH_2$ | $C_6H_{13}\overset{H}{\underset{H}{N^{\oplus}}}NHC_6H_{13}$ | $H\overset{\oplus}{N}H-CH_2-CH_2-\overset{\oplus}{N}H\begin{matrix}H\\H\end{matrix}$ |

| B-131 | B-132 | B-133 |
|---|---|---|
| $\overset{H}{\underset{H}{N^{\oplus}}}H-CH_2-CH_2-N^{\oplus}H\begin{matrix}CH_3\\CH_3\end{matrix}$ | $\begin{matrix}H_3C\\H\end{matrix}N^{\oplus}H-CH_2-CH_2-N^{\oplus}H\begin{matrix}H\\CH_3\end{matrix}$ | $\begin{matrix}H_3C\\H_3C\end{matrix}N^{\oplus}H-CH_2-CH_2-N^{\oplus}H\begin{matrix}CH_3\\CH_3\end{matrix}$ |

| B-134 | B-135 | B-136 |
|---|---|---|
| ⊕NH₃—CH₂—CH₂—NH₂ | $\begin{matrix}CH_3\\CH_3\end{matrix}N^{\oplus}H-CH_2-CH_2-NH_2$ | $\begin{matrix}H_5C_2\\H_5C_2\end{matrix}N^{\oplus}H-CH_2-CH_2-N\begin{matrix}C_2H_5\\C_2H_5\end{matrix}$ |

B-137    B-138    B-139    B-140

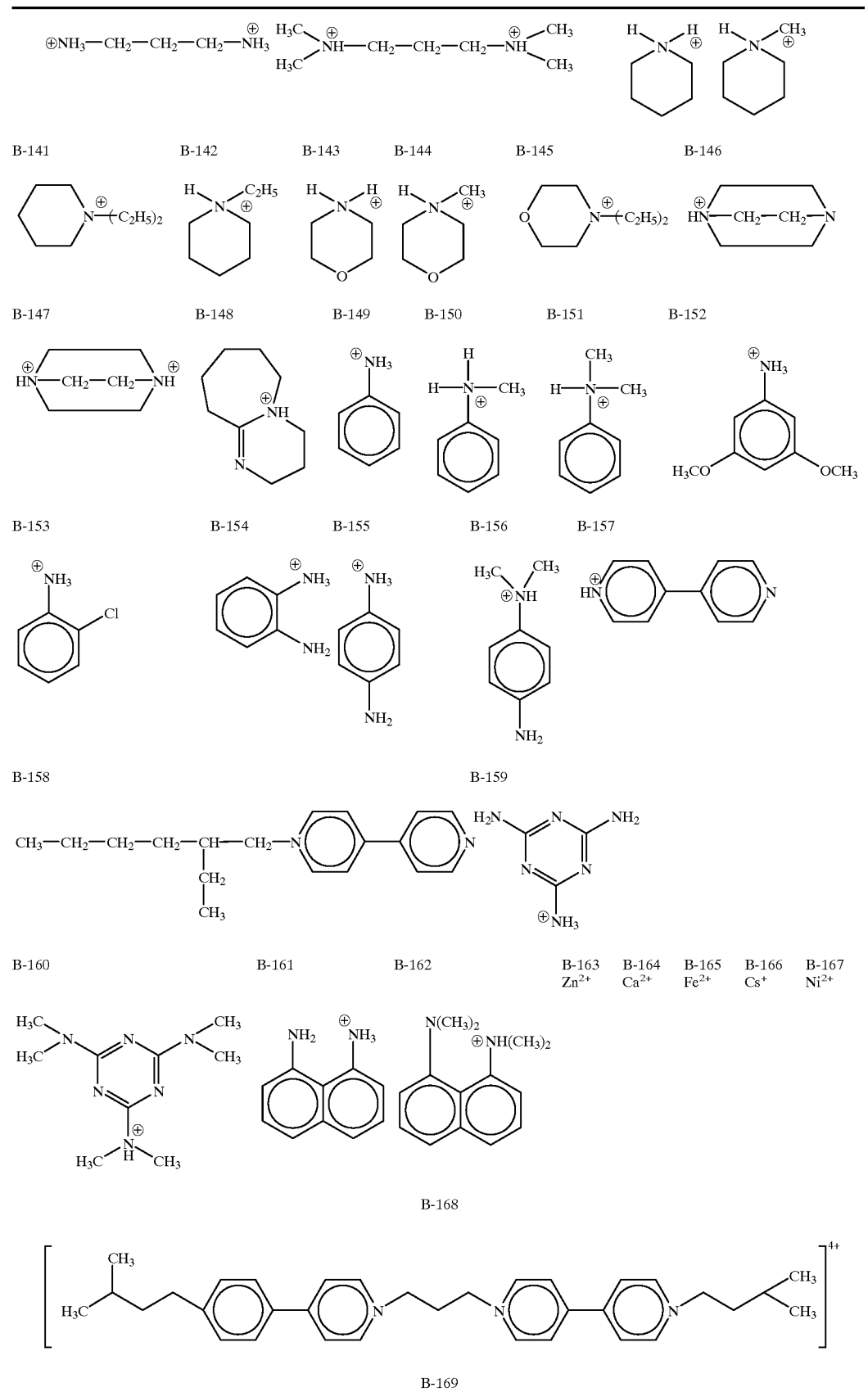

-continued
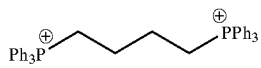
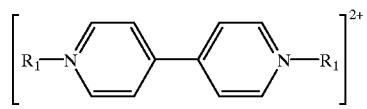
| No. | R₁ |
|---|---|
| B-170 | 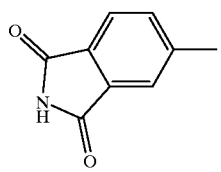 |
| B-171 | 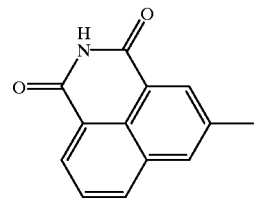 |
| B-172 | 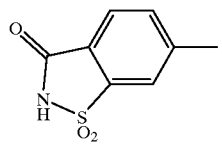 |
| B-173 | 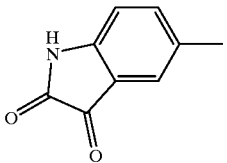 |
| B-174 | 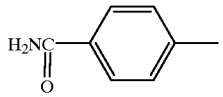 |
| B-175 | 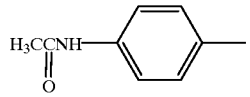 |
| B-176 | 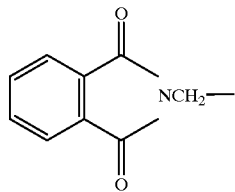 |

-continued

B-177
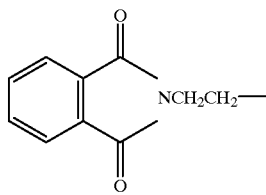

B-178
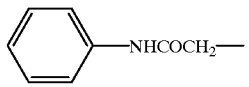

B-179    H₃CNHCOCH₂—

B-180
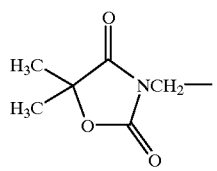

Specific examples of the compounds preferably used in the present invention are shown in Table 1 below.

In Table 1, the compounds are shown by a combination of the anion moiety and the cation moiety. For example, Dye No. 1 (anion moiety (A-4)/cation moiety (B-21)) has the following formula:

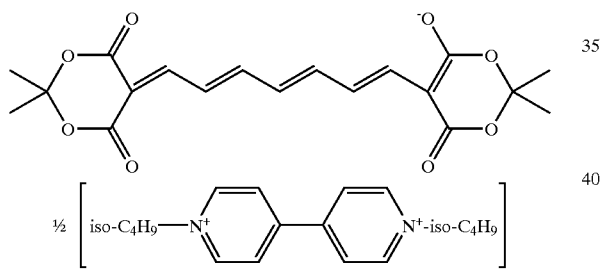

The same applies to Dye No. 2 and the followings.

TABLE 1

| Dye No. | Anion Moiety | Cation Moiety |
|---|---|---|
| 1 | A-4 | B-21 |
| 2 | A-4 | B-77 |
| 3 | A-4 | B-123 |
| 4 | A-5 | B-21 |
| 5 | A-5 | B-78 |
| 6 | A-6 | B-22 |
| 7 | A-7 | B-22 |
| 8 | A-10 | B-78 |
| 9 | A-10 | B-117 |
| 10 | A-5 | B-123 |
| 11 | A-11 | B-85 |
| 12 | A-14 | B-21 |
| 13 | A-14 | B-77 |
| 14 | A-14 | B-113 |
| 15 | A-15 | B-1 |
| 16 | A-15 | B-148 |
| 17 | A-15 | B-168 |
| 18 | A-21 | B-15 |
| 19 | A-21 | B-103 |

TABLE 1-continued

| Dye No. | Anion Moiety | Cation Moiety |
|---|---|---|
| 20 | A-23 | B-74 |
| 21 | A-24 | B-78 |
| 22 | A-25 | B-78 |
| 23 | A-28 | B-78 |
| 24 | A-33 | B-30 |
| 25 | A-33 | B-51 |
| 26 | A-34 | B-78 |
| 27 | A-36 | B-21 |
| 28 | A-36 | B-78 |
| 29 | A-36 | B-87 |
| 30 | A-37 | B-21 |
| 31 | A-37 | B-41 |
| 32 | A-37 | B-78 |
| 33 | A-37 | B-113 |
| 34 | A-37 | B-117 |
| 35 | A-38 | B-117 |
| 36 | A-38 | B-133 |
| 37 | A-38 | B-85 |
| 38 | A-39 | B-23 |
| 39 | A-39 | B-33 |
| 40 | A-39 | B-55 |
| 41 | A-39 | B-78 |
| 42 | A-39 | B-85 |
| 43 | A-39 | B-117 |
| 44 | A-39 | B-123 |
| 45 | A-39 | B-168 |
| 46 | A-40 | B-21 |
| 47 | A-40 | B-55 |
| 48 | A-40 | B-78 |
| 49 | A-40 | B-85 |
| 50 | A-40 | B-89 |
| 51 | A-40 | B-113 |
| 52 | A-40 | B-117 |
| 53 | A-40 | B-168 |
| 54 | A-41 | B-21 |
| 55 | A-44 | B-33 |
| 56 | A-44 | B-50 |
| 57 | A-44 | B-78 |
| 58 | A-44 | B-94 |
| 59 | A-44 | B-98 |
| 60 | A-44 | B-117 |
| 61 | A-44 | B-132 |
| 62 | A-45 | B-21 |

TABLE 1-continued

| Dye No. | Anion Moiety | Cation Moiety |
|---|---|---|
| 63 | A-45 | B-53 |
| 64 | A-48 | B-24 |
| 65 | A-48 | B-33 |
| 66 | A-48 | B-55 |
| 67 | A-48 | B-84 |
| 68 | A-48 | B-110 |
| 69 | A-48 | B-117 |
| 70 | A-49 | B-78 |
| 71 | A-49 | B-94 |
| 72 | A-49 | B-115 |
| 73 | A-49 | B-117 |
| 74 | A-50 | B-78 |
| 75 | A-55 | B-18 |
| 76 | A-55 | B-82 |
| 77 | A-55 | B-114 |
| 78 | A-57 | B-78 |
| 79 | A-58 | B-78 |
| 80 | A-60 | B-33 |
| 81 | A-60 | B-78 |
| 82 | A-60 | B-117 |
| 83 | A-61 | B-17 |
| 84 | A-61 | B-79 |
| 85 | A-64 | B-27 |
| 86 | A-64 | B-77 |
| 87 | A-69 | B-78 |
| 88 | A-69 | B-117 |
| 89 | A-70 | B-26 |
| 90 | A-70 | B-76 |
| 91 | A-72 | B-77 |
| 92 | A-73 | B-77 |
| 93 | A-73 | B-94 |
| 94 | A-74 | B-24 |
| 95 | A-74 | B-78 |
| 96 | A-82 | B-78 |
| 97 | A-93 | B-21 |
| 98 | A-93 | B-78 |
| 99 | A-94 | B-78 |
| 100 | A-96 | B-78 |
| 101 | A-5 | B-24 |
| 102 | A-37 | B-170 |
| 103 | A-37 | B-171 |
| 104 | A-37 | B-172 |
| 105 | A-37 | B-173 |
| 106 | A-37 | B-174 |
| 107 | A-37 | B-175 |
| 108 | A-37 | B-176 |
| 109 | A-37 | B-177 |
| 110 | A-37 | B-178 |
| 111 | A-37 | B-179 |
| 112 | A-37 | B-108 |

The 1,3-dioxane-4,6-dione nucleus for use in the present invention can be synthesized according to the method described in Chem. Ber., vol. 94, 929–943 (1961) or Tetrahedron Lett., vol. 30, 5281–5284 (1989), and conversion into an oxonol compound can be performed according to the method described in F. M. Hamer, Heterocyclic Compounds-Cyanine Dyes and Related Compounds, John Wiley & Sons, New York, London, pp. 244–247 and 463–482 (1964).

Synthesis examples of the oxonol compound represented by formula (I-1) are described below.

Synthesis Eamples

Synthesis of 1,1'-bisisobutyl-4,4'-bipyridinium dibromide 4,4'-Dipyridyl (7.8 g, 0.050 mol) and isobutyl bromide (27.4 g, 0.20 mol) were dissolved in dimethylformamide (20 ml). The mixed solution was heated to 90° C. and stirred at 90° C. for 8 hours. Thereafter, the yellow precipitate was separated by filtration and suspended in ethanol (90 ml). After adding dropwise triethylamine (2.2 ml, 0.016 mol) thereto, the suspension was stirred at room temperature for 1 hour. The yellow precipitate obtained was collected by filtration and washed with ethanol. As a result, 2.1 g of 1,1'-bisisobutyl-4,4'-bipyridinium dibromide was obtained. This corresponds to 10% of the theoretical yield.

H-NMR ($D_2O$): 9.1 (d, 4H), 8.5 (d, 4H), 4.5 (d, 4H), 2.4 (m, 2H), 1.1 (d, 12H).

Synthesis of 1,1'-bis(2,6-diethylphenyl)-4,4'-bipyridinium dichloride 1,1'-Bis(2,4-dinitrophenyl)-4,4'-bipyridinium dichloride (5.6 g, 0.010 mol) and 2,6-diethylaniline (6.6 g, 0.044 mol) were dissolved in 70% ethanol (30 ml). The mixed solution was heated under reflux for 8 hours and then the solvent was removed by evaporation. The yellow solid obtained was suspended in water (90 ml) and stirred at room temperature for 1 hour. After separating the white yellow solid by filtration, the aqueous layer was depressurized to remove the solvent by evaporation and the yellow solid obtained was washed with ethyl acetate. As a result, 4.4 g of 1,1'-bis(2,6-diethylphenyl)-4,4'-bipyridinium dichloride was obtained. This corresponds to 89% of the theoretical yield.

H-NMR ($D_2O$): 9.6 (d, 4H), 9.1 (d, 4H), 7.3–7.7 (m, 6H), 2.3 (q, 8H), 1.1 (t, 12H)

Synthesis of Dye No. 3

Meldrum's acid (2.0 g, 14.0 mmol) and N,N'-1,5-heptadiene-1-yl-7-ylidenedianiline hydrochloride (2.2 g, 7.1 mmol) were dissolved in dimethylformamide (30 ml) and thereto triethylamine (3.0 ml, 21.3 mmol) was added dropwise under ice cooling. The resulting mixed solution was stirred at room temperature for 3 hours. The reaction solution obtained was concentrated under reduced pressure and then purified by silica gel column chromatography (developed solvent: methylene chloride/methanol=4/1). As a result, 0.81 g of Dye No. 3 was obtained as violet powder. This corresponds to 24% of the theoretical yield.

H-NMR (DMSO-d6): 8.9 (s, 1H), 7.6 (d, 2H), 7.1–7.4 (m, 4H), 6.3 (dd, 1H), 3.1 (q, 6H), 1.5 (s, 12H), 1.2 (t, 9H).

λmax: 648 nm (in methanol)

Synthesis of Dye No. 1

Dye No. 3 (0.8 g, 1.7 mmol) was dissolved in methanol (30 ml) and the resulting solution was stirred at room temperature for 30 minutes. To this solution, 1,1'-bisisobutyl-4,4'-bipyridinium dibromide (0.4 g, 0.9 mmol) was added, and the mixed solution was stirred at room temperature for 4 hours. To the reaction solution, water (100 ml) was added, and the precipitate obtained was collected by filtration, washed with water and dried. As a result, 0.6 g of Dye No. 1 was obtained. This corresponds to 66% of the theoretical yield.

H-NMR (DMSO-d6): 9.4 (d, 2H), 8.8 (d, 2H), 7.6 (d, 2H), 7.1–7.4 (m, 4H), 6.3 (dd, 1H), 4.5 (d, 2H), 2.4 (m, 1H), 0.9 (d, 6H).

λmax: 648 nm (in methanol)

Synthesis of Dye No. 10

Meldrum's acid (17.2 g, 0.12 mol) and N,N'-1,3-pentadiene-1-yl-5-ylidenedianilide hydrochloride (14.2 g, 0.050 mol) were dissolved in methanol (100 ml) and thereto triethylamine (25.0 ml, 0.18 mol) of triethylamine was added dropwise under ice cooling. The resulting mixed solution was stirred at room temperature for 3 hours. After separating insoluble matters by filtration, the mother solution was concentrated under reduced pressure and then purified by silica gel column chromatography (developed solvent: methylene chloride/methanol=10/1). As a result, 13.2 g of Dye No. 10 was obtained as violet powder. This corresponds to 52% of the theoretical yield.

H-NMR (DMSO-d6): 8.9 (s, 1H), 7.7 (d, 2H), 7.5 (dd, 1H), 7.2 (dd, 2H), 3.1 (q, 6H), 1.5 (s, 12H), 1.2 (t, 9H).

λmax: 550 nm (in methanol)

Synthesis of Dye No. 5

Dye No. 10 (0.9 g, 2.0 mmol) was dissolved in methanol (30 ml) and the resulting solution was stirred at room temperature for 30 minutes. To this solution, 1,1'-bis(2,6-diethylphenyl)-4,4'-bipyridinium dichloride (0.7 g, 1.4 mmol) was added, and the mixed solution was stirred at room temperature for 4 hours. To the reaction solution, water (100 ml) was added, and the precipitate obtained was collected by filtration, washed with water and dried. As a result, 0.8 g of Dye No. 5 was obtained. This corresponds to 68% of the theoretical yield.

H-NMR (DMSO-d6): 9.6 (d, 2H), 9.1 (d, 2H), 7.7 (m, 3H), 7.5 (m, 3H), 7.2 (dd, 2H), 2.3 (q, 4H), 1.5 (s, 12H), 1.1 (t, 9H).

λmax: 550 nm (in methanol)

Synthesis of Dye No. 50

Compound a (3.9 g, 0.020 mol) shown below and N,N'-1,3-pentadiene-1-yl-5-ylidenedianiline hydrochloride (2.6 g, 9.0 mmol) were dissolved in dimethylformamide (10 ml) and thereto triethylamine (4.0 ml, 0.029 mol) of triethylamine was added dropwise under ice cooling. The resulting mixed solution was stirred at room temperature for 3 hours. The reaction solution was concentrated under reduced pressure and then purified by silica gel column chromatography (developed solvent: methylene chloride/methanol=10/1). As a result, 4.0 g of Dye No. 50 was obtained as gold powder. This corresponds to 97% of the theoretical yield.

H-NMR (DMSO-d6): 7.6 (d, 2H), 7.5 (dd, 2H), 7.2 (dd, 2H), 2.3 (m, 2H), 1.8 (m, 2H), 1.3–1.7 (m, 14H), 0.9 (d, 6H).

λmax: 553 nm (in methanol)

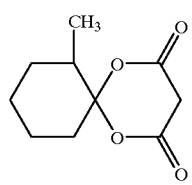

Compound a

Synthesis of Dye No. 48

Dye No. 50 (0.5 g, 1.0 mmol) was dissolved in methanol (30 ml) and thereto triethylamine (0.14 ml, 1.0 mmol) was added dropwise. The resulting solution was stirred at room temperature for 30 minutes. To this solution, 1,1'-bis(2,6-diethylphenyl)-4,4'-bipyridinium dichloride (0.35 g, 0.7 mmol) was added, and the mixed solution was stirred at room temperature for 4 hours. To the reaction solution, water (100 ml) was added, and the precipitate obtained was collected by filtration, washed with water and dried. As a result, 0.57 g of Dye No. 48 was obtained. This corresponds to 85% of the theoretical yield.

λmax: 553 nm (in methanol)

Synthesis of Dye No. 79

Compound b (1.2 g, 6.0 mmol) shown below and N,N'-1,3-pentadiene-1-yl-5-ylidenedianiline hydrochloride (0.8 g, 3.0 mmol) were dissolved in dimethylformamide (10 ml) and thereto triethylamine (1.2 ml, 9.0 mmol) of triethylamine was added dropwise under ice cooling. The resulting mixed solution was stirred at room temperature for 3 hours. The reaction solution was concentrated under reduced pressure and then purified by silica gel column chromatography (developed solvent: methylene chloride/methanol=20/1). As a result, 1.3 g of Compound c shown below was obtained as gold powder. This corresponds to 80% of the theoretical yield.

H-NMR (DMSO-d6): 8.9 (s, 1H), 7.3–7.5 (m, 13H), 6.9 (dd, 2H), 3.1 (q, 6H), 1.8 (s, 6H), 1.2 (t, 9H).

λmax: 558 nm (in methanol)

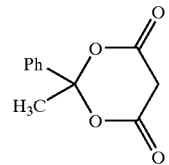

Dye Compound b

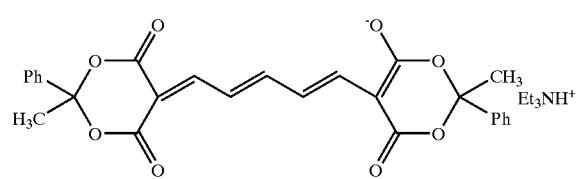

Dye Compound c

Dye Compound c (0.6 g, 1.0 mmol) was dissolved in methanol (30 ml) and the resulting solution was stirred at room temperature for 30 minutes. To this solution, 1,1'-bis(2,6-diethylphenyl)-4,4'-bipyridinium dichloride (0.3 g, 0.6 mmol) was added, and the mixed solution was stirred at room temperature for 4 hours. To the reaction solution, water (100 ml) was added, and the precipitate obtained was collected by filtration, washed with water and dried. As a result, 0.6 g of Dye No. 79 was obtained. This corresponds to 89% of the theoretical yield.

H-NMR (DMSO-d6): 9.6 (d, 2H), 9.1 (d, 2H), 7.2–7.8 (m, 15H), 6.9 (dd, 2H), 2.3 (q, 4H), 1.7 (s, 6H), 1.1 (t, 6H).

λmax: 558 nm (in methanol)

The dye compounds represented by formula (I-1) according to the present invention may be used either individually or in combination of two or more thereof. The dye compound represented by formula (I-1) may also be used in combination with another dye compound conventionally known as a dye compound for information recording mediums.

Examples of the another dye compound include oxonol-based dyes, cyanine-based dyes, azo metal complexes, phthalocyanine-based dyes, pyrylium-based dyes, thiopyrylium-based dyes, azulenium-based dyes, squarylium-based dyes, naphthoquinone-based dyes, triphenylmethane-based dyes and triallylmethane-based dyes, exclusive of those for use in the present invention.

The information recording medium of the present invention comprises a transparent disc-like substrate having provided thereon a recording layer, the disc-like substrate having a diameter of 120±3 mm or 80±3 mm and a thickness of 0.6±0.1 mm and having formed thereon a pregroove in a track pitch of from 0.6 to 0.9 μm, and the recording layer comprising the dye compound represented by formula (I-1) and being provided on the side having the pregroove of the substrate.

In the information recording medium of the present invention, a reflection layer is preferably further provided on the recording layer. Furthermore, a protective layer may be provided on the reflection layer.

To state specifically, the preferred embodiments of the information recording medium of the present invention are as follows:

(1) an information recording medium having a thickness of 1.2±0.2 mm, obtained by combining two sheets of laminates each comprising a transparent disc-like substrate having provided thereon a recording layer such that respective recording layers are disposed in the inner side, the disc-like substrate having a diameter of 120±3 mm or 80±3 mm and a thickness of 0.6±0.1 mm and having formed thereon a pregroove in a track pitch of from 0.6 to 0.9 μm, and the recording layer comprising the dye compound represented by formula (I-1) according to the present invention and being provided on the side having the pregroove of the substrate; and (2) an information recording medium having a thickness of 1.2±0.2 mm, obtained by combining a laminate comprising a transparent disc-like substrate having provided thereon a recording layer with a disc-like protective sheet having almost the same dimension as the disc-like substrate such that the recording layer is disposed in the inner side, the disc-like substrate having a diameter of 120±3 mm or 80±3 mm and a thickness of 0.6±0.1 mm and having formed thereon a pregroove in a track pitch of from 0.6 to 0.9 μm, and the recording layer comprising the dye compound represented by formula (I-1) according to the present invention and being provided on the side having the pregroove of the substrate.

In these embodiments, it is also preferred to provide a reflection layer on the recording layer. Furthermore, a protective layer may be further provided on the reflection layer.

The production method of the information recording medium of the present invention is described below.

The information recording medium of the present invention can be fundamentally produced using the materials for use in the production of CD-R type information recording mediums except that a substrate having formed thereon a pregroove in a track pitch narrower than that of CD-R is used so as to achieve higher recording density. More specifically, the DVD-R type information recording medium can be produced by preparing two sheets of laminates each comprising a substrate having formed thereon in sequence a recording layer, a reflection layer and if desired, a protective layer, and combining these two sheets while disposing recording layers in the inner side, or by combining the laminate with a disc-like protective substrate having almost the same dimension as the substrate of the laminate, using an adhesive.

The information recording medium of the present invention may be produced, for example, by the following method.

The substrate (including the protective substrate) can be freely selected from various materials conventionally used as the substrate of information recording mediums. Examples of the substrate material include glass; polycarbonate; acrylic resin such as polymethyl methacrylate; vinyl chloride-based resin such as polyvinyl chloride and vinyl chloride polymer; epoxy resin; and amorphous polyolefin and polyester. Two or more of these materials may be used in combination, if desired. The substrate material may be used as a film or a rigid substrate. Among the above-described materials, carbonate is preferred in view of humidity resistance, dimensional stability and cost.

On the side having provided thereon the recording layer of the substrate, an undercoat layer may be provided for the purpose of improving planarity, increasing adhesive strength and preventing deterioration of the recording layer. Examples of the material for the undercoat layer include polymer materials such as polymethyl methacrylate, an acrylic acid-methacrylic acid copolymer, a styrene-maleic acid anhydride copolymer, polyvinyl alcohol, N-methylolacrylamide, a styrene-vinyl toluene copolymer, chlorosulfonated polyethylene, nitrocellulose, polyvinyl chloride, chlorinated polyolefin, polyester, polyimide, a vinyl acetate-vinyl chloride copolymer, an ethylene-vinyl acetate copolymer, polyethylene, polypropylene and polycarbonate; and surface modifiers such as silane coupling agent.

The undercoat layer may be formed by dissolving or dispersing the above-described substance in an appropriate solvent to prepare a coating solution and then coating the coating solution on the substrate surface by a coating method such as spin coating, dip coating or extrusion coating.

The undercoat layer generally has a thickness of from 0.005 to 20 μm, preferably from 0.01 to 10 μm.

On the substrate (or undercoat layer), grooves for tracking or irregularities (pregrooves) showing the information such as address signal are formed. This pregroove is preferably formed directly on the substrate to have the above-described track pitch at the time of injection molding or extrusion molding a resin material such as polycarbonate.

The pregroove may also be formed by providing a pregroove layer. As the material for the pregroove layer, a mixture of at least one monomer (or oligomer) selected from a monoester, a diester, a triester and a tetraester of an acrylic acid, with a photopolymerization initiator may be used.

The pregroove layer may be formed, for example, by coating a mixed solution consisting of the above-described acrylic acid ester and a polymerization initiator on a precisely manufactured matrix (stamper), overlaying a substrate on the coated layer, irradiating an ultraviolet ray through the substrate or matrix to cure the coated layer and thereby fix the substrate with the coated layer, and then peeling off the substrate from the matrix.

The pregroove layer generally has a thickness of from 0.05 to 100 μm, preferably from 0.1 to 50 μm.

The pregroove preferably has a depth of from 300 to 2,000 Å and a half value width of from 0.2 to 0.9 μm. The depth of the pregroove layer is preferably from 1,500 to 2,000 Å, because the sensitivity can be improved while causing almost no reduction in the reflectance. Thus, such an optical disc (an optical disc comprising a deeply pregrooved substrate having formed thereon a recording layer comprising a dye represented by formula (I-1) or (I-2)) has a high sensitivity. By virtue of this high sensitivity, recording can be performed with a low laser power and in turn an inexpensive semiconductor laser can be used or the use life of the semiconductor laser can be elongated.

On the side having the pregroove of the substrate (or on the undercoat layer), a recording layer comprising the dye compound represented by the formula according to the present invention is provided.

The recording layer may contain a compound of various types conventionally known as the singlet oxygen quencher so as to further improve the light fastness. Representative examples of the quencher include metal complexes, diimmonium salts and ammonium salts represented by formulae (III), (IV) and (V) of JP-A-3-224793, and nitroso compounds described in JP-A-2-300287 and JP-A-2-300288.

The recording layer may be formed by dissolving the dye according to the present invention and if desired, a quencher and a binder in a solvent to prepare a coating solution, coating this coating solution on the substrate surface to form a film, and then drying the film.

Examples of the solvent for use in the coating solution for forming the dye recording layer include esters such as butyl acetate and cellosolve acetate; ketones such as methyl ethyl ketone, cyclohexanone, methyl isobutyl ketone; chlorinated hydrocarbons such as dichloromethane, 1,2-dichloroethane and chloroform; amides such as dimethylformamide; hydrocarbons such as cyclohexane; ethers such as tetrahydrofuran, ethyl ether and dioxane; alcohols such as ethanol, n-propanol, isopropanol, n-butanol and diacetone alcohol; fluorine-based solvents such as 2,2,3,3-tetrafluoropropanol; and glycol ethers such as ethylene glycol monomethyl ether, ethylene glycol monoethyl ether and propylene glycol monomethyl ether. These solvents may be used individually or in combination of two or more thereof by taking account of the solubility of the compound used.

The coating solution for the recording layer may further contain various additives such as antioxidant, UV absorber, plasticizer and lubricant, according to the purposes.

Examples of the binder include natural organic polymer materials such as gelatin, cellulose derivative, dextran, rosin and rubber, and synthetic organic polymers such as an initial condensate of a thermosetting resin. Examples of the thermosetting resin include hydrocarbon-based resins such as polyethylene, polypropylene, polystyrene and polyisobutylene; vinyl-based resins such as polyvinyl chloride, polyvinylidene chloride and a polyvinyl chloride-polyvinyl acetate copolymer; acrylic resins such as polymethyl acrylate and polymethyl methacrylate; polyvinyl alcohol; chlorinated polyethylene; epoxy resin; butyral resin; rubber derivatives; and phenol-formaldehyde resin.

In the case of using a binder in combination as the material of the recording layer, the amount of the binder used is generally from 0.01 to 50 times (by weight), preferably from 0.1 to 5 times (by weight), based on the dye.

The thus-prepared coating solution generally has a concentration of from 0.01 to 10 wt %, preferably from 0.1 to 5 wt %.

Examples of the coating method include a spray coating method, a spin coating method, a dip coating method, a roll coating method, a blade coating method, a doctor roll coating method and a screen printing method.

The recording layer may consist of a single layer or multiple layers. The thickness of the recording layer is generally from 20 to 500 nm, preferably from 50 to 300 nm.

On the recording layer, a reflection layer is provided so as to improve the reflectance at the reproduction of the information.

The photoreflective substance as the material of the reflection layer is a substance having a high reflectance to a laser ray and examples thereof include metals and semimetals, such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn and Bi, and stainless steel. Among these, preferred are Cr, Ni, Pt, Cu, Ag, Au, Al and stainless steel. These substances may be used either individually or in combination of two or more thereof, or may also be used as an alloy.

The reflection layer may be formed, for example, by evaporating, sputtering or ion-plating the above-described reflective substance on the recording layer. The reflection layer generally has a thickness of from 10 to 300 nm, preferably from 50 to 200 nm.

On the reflection layer, a protective layer may be provided for the purpose of physically or chemically protecting the recording layer and the like. The protective layer may also be provided on the side having not provided thereon the recording layer of the substrate so as to increase the scratch resistance and the humidity resistance.

Examples of the material for use in the protective layer include inorganic substances such as SiO, $SiO_2$, $MgF_2$, $SnO_2$ and $Si_3N_4$, and organic substances such as thermoplastic resin, thermosetting resin and UV-curable resin.

The protective layer may be formed, for example, by laminating a film obtained by the extrusion of a plastic on the reflection layer and/or the substrate through an adhesive layer, or may also be formed using a technique of vacuum evaporation, sputtering or coating. In the case of a thermoplastic resin or thermosetting resin, the protective layer may be formed by dissolving the resin in an appropriate solvent to prepare a coating solution, coating the coating solution and then drying it. In the case of a UV-curable resin, the protective layer may be formed by coating the resin as it is or coating a coating solution prepared by dissolving the resin in an appropriate solvent, and then irradiating an UV ray thereon to cure the resin. The coating solution may further contain various additives such as antistatic agent, antioxidant and UV absorber, according to the purposes.

The protective layer generally has a thickness of from 0.1 to 100 $\mu$m.

After passing through the above-described steps, a laminate comprising a substrate having provided thereon a recording layer, a reflection layer and if desired, a protective layer is manufactured.

Two sheets of laminates thus produced are attached together using an adhesive such that respective recording layers are disposed in the inner side. As a result, a DVD-R type information recording medium having two recording layers can be produced.

The laminates may be attached together using a slowly active UV-curable adhesive, by a hot melt method, or with a pressure sensitive adhesive tape, however, in view of the damage on the recording layer or cost, a method of using a slowly active UV-curable adhesive is preferred. The adhesive used is preferably a solvent-free adhesive.

The adhesive may be coated by spray coating, spin coating, roll coating or screen printing, preferably by screen printing.

When the laminate obtained as above is attached using an adhesive together with a disc-like protective substrate having almost the same dimension as the substrate of the laminate such that the recording layer is disposed in the inner side, a DVD-R type information recording medium having a recording layer only on a single side may be produced.

The information recording method using the above-described information recording medium of the present invention is described below.

While rotating the information recording medium at a constant linear velocity (in the case of CD format, from 1.2 to 14 m/sec) or a constant angular velocity, a laser ray for recording, such as a semiconductor laser ray, is irradiated from the substrate side. Upon irradiation of the light, cavities are formed on the interface between the recording layer and the reflection layer (the formation of cavities is accompanied by the deformation of either one or both of the recording layer and the reflection layer), the substrate is deformed to have a padded portion, or the recording layer is discolored or varied in the association state, as a result, it is considered that the refractive index changes and thereby the information is recorded. The recording light used is a laser ray in the visible region or a semiconductor laser beam having an oscillation wavelength of generally from 600 to 700 nm (preferably from 620 to 680 nm, more preferably from 630 to 650 nm).

The thus-recorded information can be reproduced by irradiating a semiconductor laser ray having the same wavelength as that used at the recording from the substrate side while rotating the information recording medium at the same constant linear velocity as above, and detecting the reflected light.

The present invention is described in greater detail below by referring to the Examples, however, the present invention should not be construed as being limited thereto.

EXAMPLE 1

Manufacturing of Optical Recording Medium

A substrate having a thickness of 0.6 mm and a diameter of 120 mm and having thereon a spiral groove (depth: 156 nm, width: 290 nm, track pitch: 0.74 µm) was formed from a polycarbonate resin using an injection molding machine (manufactured by Sumitomo Jukikai Kogyo KK).

2.0 g of Dye No. 5 was dissolved in 100 ml of 2,2,3,3-tetrafluoropropanol to prepare a coating solution and the coating solution was coated on the side having the groove of the substrate prepared above by a spin coating method to form a dye layer. At this time, the dye layer had a thickness of 150 nm.

On the dye coated surface, silver was sputtered to form a reflection layer having a thickness of about 150 nm. Subsequently, an ultraviolet-curable resin (DICURE CLEAR SD-318, produced by Dai-Nippon Ink & Chemicals, Inc.) was coated on the reflection layer formed by a spin coating method. Then, an ultraviolet ray was irradiated thereon from a metal halide lamp to form a protective layer of about 7 µm, thereby obtaining Disc A having a thickness of 0.6 mm.

Separately, silver was sputtered on the substrate prepared above to form a protective layer without passing through the coating of a dye and thereby 0.6 mm-thick Disc B having no dye recording layer was obtained.

Disc A and Disc B were attached together and processed as follows to finish one sheet of disc. On respective protective layers of Disc A and Disc B, a slowly active cationic polymerization-type adhesive (SK7000, produced by Sony Chemical KK) was coated by screen printing. The screen printing plate used had a mesh size of 300 mesh. Thereafter, an ultraviolet ray was irradiated from a metal halide lamp and immediately thereafter, the protective layer sides of Disc A and Disc B were attached together and compressed from both sides. After standing for about 5 minutes, the adhesive was completely cured and one sheet of disc having a thickness of 1.2 mm was finished.

EXAMPLES 2 TO 8

Discs were obtained thoroughly in the same manner as in Example 1 except that the dyes shown in Table 2 according to the present invention were used in the same amount in place of Dye No. 5 in Example 1.

Comparative Example 1

A disc was finished thoroughly in the same manner as in Example 1 except that 1.0 g of Comparative Dye A in Table 2 was dissolved in 100 ml of 2,2,3,3-tetrafluoropropanol. At this time, the dye layer had a thickness of 100 nm.

Comparative Example 2

A disc was finished thoroughly in the same manner as in Example 1 except that 4.0 g of Comparative Dye D in Table 2 was dissolved in 100 ml of 2,2,3,3-tetrafluoropropanol. At this time, the dye layer had a thickness of 300 nm.

Comparative Example 3 to 5

Discs were obtained thoroughly in the same manner as in Example 1 except for using Comparative Dyes J to L in Table 2.

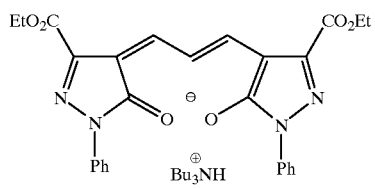

Comparative Dye A

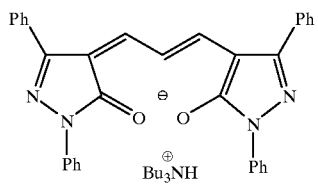

Comparative Dye D

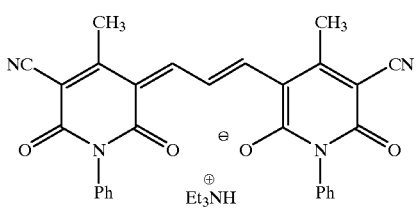

Comparative Dye J

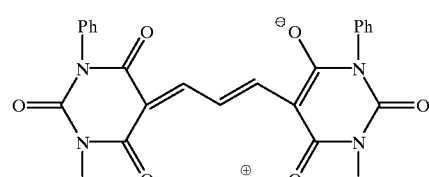

Comparative Dye K

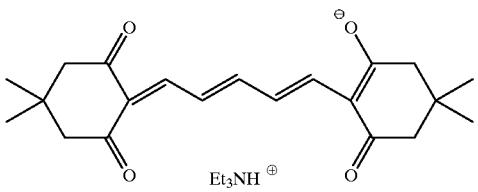

Comparative Dye L

Evaluation as Optical Disc

A 8-16 modulated signal was recorded on the DVD-R type optical discs obtained above in the Examples and Comparative Examples at a constant linear velocity of 3.49 m/s and a recording power of 9 mW with a laser ray having a wavelength of 635 nm (pick up at NA of 0.6) using an evaluation machine DDU1000 (manufactured by Balsteck KK). Thereafter, the signal was reproduced at a laser power of 0.5 mW using a laser ray having the same wavelength as the recording laser ray and the 3T jitter and reflectance were measured.

The reflectance was determined by measuring the return light intensity at the tracking on the groove. The dispersion in the pit signal length was determined using a time interval analyzer and its standard deviation σ was shown as the jitter.

TABLE 2

|  | Example | | | | | | | | Comparative Example | | | | |
| --- | --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 | 5 |
| Dye | No. 5 | No. 10 | No. 48 | No. 46 | No. 52 | No. 79 | No. 66 | No. 92 | A | D | J | K | L |
| n | 2.3 | 2.35 | 2.33 | 2.24 | 2.26 | 2.31 | 2.28 | 2.27 | 2.3 | 2.24 | 2.4 | 2.43 | 2.41 |
| k | 0.06 | 0.05 | 0.06 | 0.06 | 0.06 | 0.05 | 0.04 | 0.06 | 0.06 | 0.06 | 0.06 | 0.1 | 0.09 |
| Layer thickness | 150 | 150 | 150 | 150 | 150 | 150 | 150 | 150 | 90 | 300 | 150 | 150 | 150 |
| Jitter | 10.5 | 10.2 | 9.8 | 10.7 | 10.8 | 10.6 | 10.9 | 10.4 | 13.2 | 14.8 | 13.5 | 14.1 | 13.7 |
| Reflectance | 57 | 62 | 58 | 59 | 57 | 61 | 63 | 59 | 48 | 51 | 57 | 41 | 48 |

It is seen from the results in Table 2 that the DVD-R type optical discs according to the present invention (Examples 1 to 8) exhibited high reflectance and low jitter, revealing that the discs have excellent recording and reproduction properties. On the other hand, comparative DVD-R type discs (Comparative Examples 1 to 5) failed in giving sufficiently high performance particularly with respect to the jitter, accordingly, the recording and reproduction properties thereof are not satisfied by any means and, for example, errors readily occur in the reading of the digital signal. Also, in the case where the reflectance is low as in Comparative Examples 1, 4 and 5, the signal intensity decreases at the reading of the signal and errors readily occur in the reading of the digital signal, thus, the recording and reproduction properties cannot be satisfied.

By using a specific dye compound represented by the formula above where a Meldrum's acid derivative is introduced, a DVD-R type information recording medium having excellent recording properties afforded with high reflectance and low jitter can be obtained. In particular, by using the dye compound according to the present invention, the jitter can be reduced as compared with conventional optical recording mediums and accordingly, an image recording medium suitable particularly for the DVD-R type can be produced.

While the invention has been described in detail and with reference to specific embodiments thereof, it will be apparent to one skilled in the art that various changes and modifications can be made therein without departing from the spirit and scope thereof.

What is claimed is:

1. An oxonol compound represented by formula (I-3):

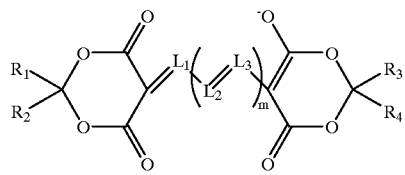

(I-3)

-continued $$\left[ \begin{array}{c} R_{15}-N \diagup\!\!\!\diagdown\!\!\!\diagup\!\!\!\diagdown N-R_{16} \\ (R_{13})_r \quad (R_{14})_s \end{array} \right]^{k+}_{1/k}$$

wherein $R_1$, $R_2$, $R_3$ and $R_4$ each independently represents a hydrogen atom, a substituted or unsubstituted alkyl group, a substituted or unsubstituted aryl group, a substituted or unsubstituted aralkyl group or a substituted or unsubstituted heterocyclic group, $L_1$, $L_2$ and $L_3$ each independently represents a methine group which may have a substituent, m represents 0, 1, 2 or 3, $R_{13}$ and $R_{14}$ have the same meanings as the groups represented by $R_5$ and $R_6$ in formula (I-2), respectively, $R_{15}$ and $R_{16}$ each independently represents a substituted or unsubstituted alkyl group having from 1 to 18 carbon atoms, a substituted or unsubstituted alkenyl group having from 2 to 18 carbon atoms, a substituted or unsubstituted alkynyl group having from 2 to 18 carbon atoms, a substituted or unsubstituted aralkyl group having from 7 to 18 carbon atoms, a substituted or unsubstituted aryl group having from 6 to 18 carbon atoms or a substituted or unsubstituted 4-, 5-, 6- or 7-membered heterocyclic group, the couples of $R_{13}$ and $R_{14}$, $R_{13}$ and $R_{15}$, $R_{14}$ and $R_{16}$, and $R_{15}$ and $R_{16}$ each may be combined to form a 4-, 5-, 6- or 7-membered ring, r and s each independently represents 0 or an integer of from 1 to 4 and k represents an integer of from 1 to 10, provided that when r and s each is 2 or more, the plurality of $R_{13}$ or $R_{14}$ groups may be the same or different, and when m is 2 or 3, the plurality of $L_2$ and $L_3$ groups may be the same or different.

* * * * *